United States Patent
Rogers et al.

(10) Patent No.: US 6,217,331 B1
(45) Date of Patent: Apr. 17, 2001

(54) SINGLE-STAGE IMPLANT SYSTEM

(75) Inventors: Dan Paul Rogers, Royal Palm Beach; Gale R. Brown, Palm City; Ralph E. Goodman, West Palm Beach; Richard J. Lazzara, Lake Worth, all of FL (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 0 days.

(21) Appl. No.: 09/164,934

(22) Filed: Oct. 1, 1998

Related U.S. Application Data

(60) Provisional application No. 60/061,076, filed on Oct. 3, 1997, provisional application No. 60/060,801, filed on Oct. 3, 1997, and provisional application No. 60/074,404, filed on Feb. 11, 1998.

(51) Int. Cl.$^7$ .................................................. A61C 8/00
(52) U.S. Cl. .......................................... 433/173; 433/174
(58) Field of Search .................................... 433/173, 174

(56) References Cited

U.S. PATENT DOCUMENTS

| D. 296,362 | 6/1988 | Branemark | D24/33 |
| 4,547,157 | 10/1985 | Driskell | 433/173 |
| 4,624,673 | 11/1986 | Meyer | 623/16 |

(List continued on next page.)

FOREIGN PATENT DOCUMENTS

| 679 117 A5 | 12/1991 | (CH) | A61C/8/00 |
| 0 727 193 A1 | 8/1996 | (EP) . | |
| 2 252 501 | 8/1992 | (GB) | A61C/8/00 |
| WO 96/19946 | 7/1996 | (WO) | A61C/7/00 |
| WO 96/19947 | 7/1996 | (WO) | A61C/8/00 |
| WO 96/29019 | 9/1996 | (WO) | A61C/8/00 |
| WO 96/29020 | 9/1996 | (WO) | A61C/8/00 |
| WO 97/01306 | 1/1997 | (WO) . | |
| WO 97/06930 | 2/1997 | (WO) | B25B/23/10 |
| WO 97/14371 | 4/1997 | (WO) | A61C/8/00 |
| WO 97/20518 | 6/1997 | (WO) | A61C/8/00 |
| WO 97/27816 | 8/1997 | (WO) . | |
| WO 97/28755 | 8/1997 | (WO) | A61C/9/00 |
| WO 97/28756 | 8/1997 | (WO) | A61C/9/00 |
| WO 98/31296 | 7/1998 | (WO) | A61C/8/00 |
| WO 98/36701 | 8/1998 | (WO) | A61C/8/00 |

OTHER PUBLICATIONS

Astra Tech Inc., "Astra Tech Implants: Dental System," 19 pages, (No Date).

Ledermann et al., "The Ha–Ti Implant," Schweiz Monatsschr Zahnmed, vol. 101, No. 5, 1991, pp. 611–617.

Sutter et al., "The New Restorative Concept of the ITI Dental Implant System: Desing and Engineering," *The Int'l Journal of Periodontics& Restorative Dentistry*, vol. 13, No. 5, 1993, pp. 410–431.

*Primary Examiner*—Ralph A. Lewis
(74) *Attorney, Agent, or Firm*—Jenkens & Gilchrist

(57) ABSTRACT

A single stage dental implant for implantation in living jawbone having overlying gingiva comprises a generally cylindrical body section having an exterior surface for confronting the jawbone and a head section attached to the body section for extending through the overlying gingiva when the body section is confronting the jawbone. The head section has an end portion which is generally near an outer layer of the gingiva. The implant further includes a bore within the head section extending to an opening at the end portion of the head section. The bore is defined by first, second, and third walls. The first wall has internal threads. The second wall has a larger diameter than the first surface and is substantially cylindrical. The second wall extends from the first wall toward the end portion. The third wall extends from the second wall to the opening and flares toward the opening to a diameter that is wider than a diameter of the second wall. The implant is delivered to the site in the patient's mouth with a carrier that is expanded into the second wall of the bore thereby developing a tight engagement capable of withstanding the insertion torque. The implant can be fitted with posts which extend above the upper portion of the implant. The post can be fitted with gingival forming components and temporary posts.

39 Claims, 22 Drawing Sheets

U.S. PATENT DOCUMENTS

| | | | |
|---|---|---|---|
| 4,722,688 | 2/1988 | Lonca | 433/173 |
| 4,772,204 | 9/1988 | Söderberg | 433/174 |
| 4,826,434 | 5/1989 | Krueger | 433/174 |
| 4,960,381 | 10/1990 | Niznick | 433/174 |
| 5,000,685 | 3/1991 | Brajnovic | 433/173 |
| 5,022,860 | 6/1991 | Lazzara et al. | 433/174 |
| 5,030,096 | 7/1991 | Hurson et al. | 433/173 |
| 5,061,181 | 10/1991 | Niznick | 433/174 |
| 5,062,800 * | 11/1991 | Niznick | 433/173 |
| 5,199,873 | 4/1993 | Schulte et al. | 433/174 |
| 5,205,745 | 4/1993 | Kamiya et al. | 433/173 |
| 5,286,195 * | 2/1994 | Clostermann | 433/173 |
| 5,297,963 | 3/1994 | Dafatry | 433/172 |
| 5,316,476 | 5/1994 | Krauser | 433/173 |
| 5,316,477 | 5/1994 | Calderon | 433/173 |
| 5,322,443 | 6/1994 | Beaty | 433/141 |
| 5,328,371 * | 7/1994 | Hund et al. | 433/173 |
| 5,350,302 | 9/1994 | Marlin | 433/174 |
| 5,362,237 | 11/1994 | Chalifoux | 433/220 |
| 5,368,483 | 11/1994 | Sutter et al. | 433/173 |
| 5,399,090 | 3/1995 | Padros-Fradera | 433/173 |
| 5,433,606 | 7/1995 | Niznick et al. | 433/173 |
| 5,437,550 | 8/1995 | Beaty et al. | 433/141 |
| 5,458,488 | 10/1995 | Chalifoux | 433/173 |
| 5,478,237 | 12/1995 | Ishizawa | 433/201.1 |
| 5,489,210 | 2/1996 | Hanosh | 433/173 |
| 5,503,558 | 4/1996 | Clokie | 433/173 |
| 5,533,898 | 7/1996 | Mena | 433/173 |
| 5,564,923 | 10/1996 | Grassi et al. | 433/173 |
| 5,573,401 | 11/1996 | Davidson et al. | 433/201.1 |
| 5,588,838 | 12/1996 | Hansson et al. | 433/173 |
| 5,636,989 | 6/1997 | Somborac et al. | 433/173 |
| 5,639,237 * | 6/1997 | Fontenot | 433/173 |
| 5,642,996 | 7/1997 | Mochida et al. | 433/174 |
| 5,651,675 | 7/1997 | Singer | 433/172 |
| 5,683,249 | 11/1997 | Ibsen et al. | 433/201.1 |
| 5,695,336 | 12/1997 | Lazzara et al. | 433/173 |
| 5,702,346 | 12/1997 | Lazzara et al. | 433/173 |
| 5,709,547 | 1/1998 | Lazzara et al. | 433/174 |
| 5,725,375 | 3/1998 | Rogers | 433/172 |
| 5,727,943 | 3/1998 | Beaty et al. | 433/174 |
| 5,749,732 | 5/1998 | Sendax | 433/174 |
| 5,752,830 | 5/1998 | Suarez | 433/173 |
| 5,759,034 | 6/1998 | Daftary | 433/173 |
| 5,762,500 | 6/1998 | Lazarof | 433/213 |
| 5,782,637 | 7/1998 | Cosenza | 433/173 |
| 5,782,918 * | 7/1998 | Klardie et al. | 433/173 |
| 5,823,777 | 10/1998 | Misch et al. | 433/174 |
| 5,829,977 | 11/1998 | Rogers et al. | 433/172 |
| 5,842,864 | 12/1998 | Unger | 433/172 |

* cited by examiner

*Fig. 19*
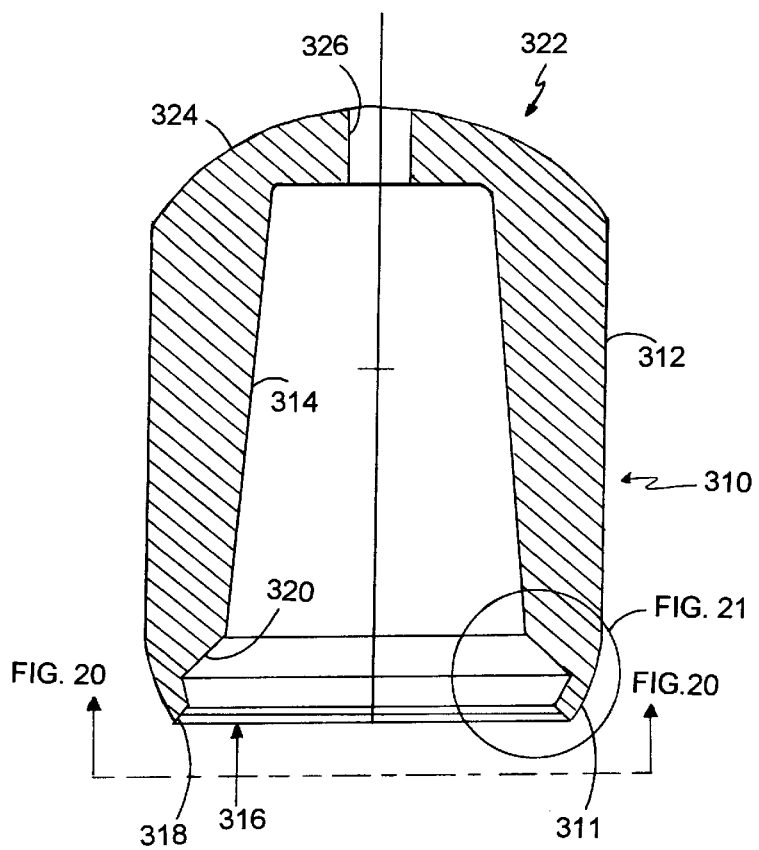
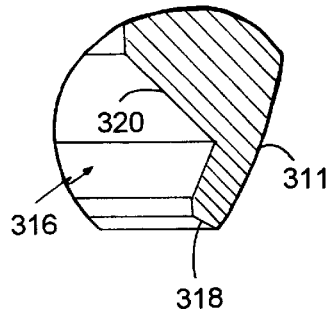
*Fig. 21*
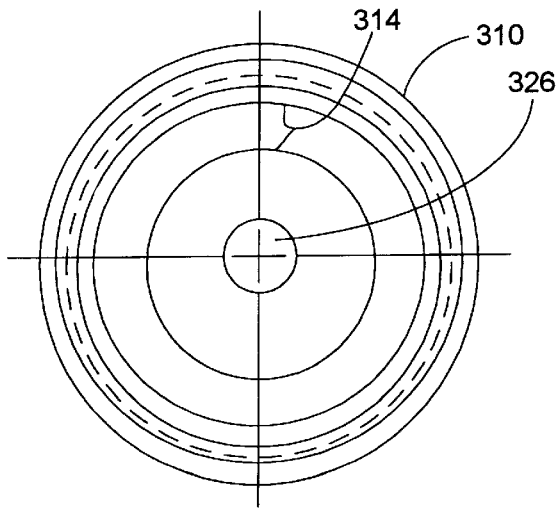
*Fig. 20*

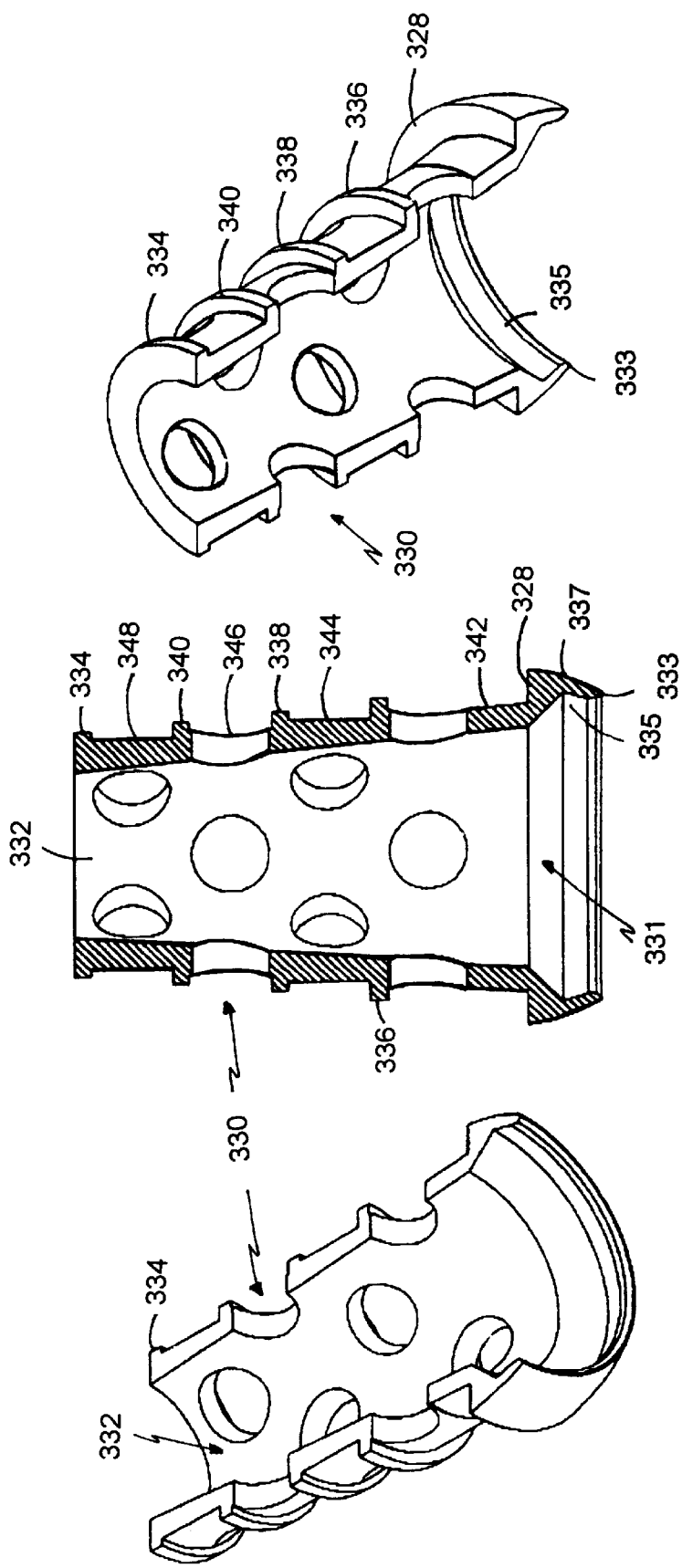

SINGLE-STAGE IMPLANT SYSTEM

This application claims benefit of provisional application Ser. No. 60/061,076 filed Oct. 3, 1997, also Ser. No. 60/060,801 filed Oct. 3, 1997 and Ser. No. 60/074,404 filed Feb. 11, 1998.

FIELD OF THE INVENTION

The invention relates generally to implants and, in particular, a single-stage dental implant that promotes healing of the gingiva and osseointegration simultaneously.

BACKGROUND OF THE INVENTION

It is becoming more common to replace a missing tooth with a prosthetic tooth that is placed upon and attached to a dental implant. The dental implant serves as the artificial root in that it integrates with the jawbone. The prosthetic tooth preferably has a size and a color that mimics the missing natural tooth. Consequently, the patient has an aesthetically pleasing and structurally sound artificial tooth.

Current methods by which the prosthetic tooth and implant are completely integrated into the patient's mouth require six to ten months, and sometimes longer, because two distinct, time-consuming steps are involved. First, the implant is inserted into the jawbone and covered by suturing the overlying gingival tissue. Covering the implant with the overlying gingiva is needed to minimize the likelihood of infection around the implant. Covering the implant also helps to guard against any disturbances of the implant that may slow its rate of osseointegration. The implant then osseointegrates with the jawbone for a period, usually in the range of three to six months.

After osseointegration is complete, the second step is encountered in which the gingiva is again cut open and a healing abutment is placed onto the implant. The overlying gingiva is sutured to allow it to properly heal around the healing abutment. Thus, when the prosthetic tooth is eventually placed upon the implant, the gingiva nicely conforms around the prosthetic tooth. However, it typically takes four to eight weeks before the gingiva is healed and the prosthetic tooth can be placed on the implant to complete the overall process. These implants can be referred to as "subgingival implants."

Single-stage implants or "transgingival implants" simultaneously promote osseointegration and the healing of the gingiva. This is accomplished by providing an implant that has a portion that integrates with the jawbone and a portion that extends through the overlying gingiva so that the gingiva properly heals therearound. Thus, the four to eight week gingival healing process occurs during the three to six month period of osseointegration. Consequently, the patient is fitted with a prosthesis in a shorter period of time. And, the gingiva is lacerated and sutured one less time compared with two-stage systems which reduces the trauma to that region, the discomfort experienced by the patient, and the overall cost because the number of dental procedures is minimized.

It is sometimes desirable to convert a subgingival implant to the configuration of a transgingival style or vice versa. For example, if one style is best suited for installation in a first site in a patient's jawbone, but another style is best suited for installation in another site, the restoring dentist seeking to fashion a bridge supported on implants installed in both sites might prefer to convert one style to the other in order to make the bridge using common components. Similarly, if a restoring dentist has on hand implants of one style and components for a new improved style become available, for reasons of economy it might be desirable to convert the available implants to the new styles so they can be used with the new components. However, known transition components introduce gaps between the components and present alignment problems for the restoration components.

Furthermore, during the preparation of dental restorations supported on artificial roots implanted in living jawbone, it is frequently useful to provide a temporary cover for a post or abutment (that eventually holds the artificial dentition) supported on a transgingival implant. It is also desirable to prevent the gingival tissue from collapsing around the transgingival implant or to maintain an opening in the tissue at least until temporary dentition is made. This invention also relates to a temporary cap useful to cover such abutments and posts for a transgingival implant.

SUMMARY OF THE INVENTION

The single-stage dental implant is typically installed through a ridge in the jawbone that is covered by gingival tissue. The dental implant provides an artificial root on which a prosthetic tooth is mounted to replace a missing tooth which formerly emerged from the jawbone. The single-stage implant comprises an anchoring portion for extending into and integrating with the jawbone and an integral gingival section that extends beyond the ridge of the jawbone. Because the gingival section is integral with the anchoring portion, there is no seam in which bacteria may collect to cause infections.

The implant has various embodiments with various internal structures which allow the implant to be driven into the bone tissue in the patient's mouth. These internal structures typically engage a carrier that is delivered with the implant. Thus, the clinician uses tools that engage the carrier to drive the implant to the appropriate depth. After insertion, the clinician removes the carrier from the implant and a cover screw is placed thereover. The implant also has structural features enhancing its ability to support the artificial dentition on the post.

The inventive single-stage system also includes conversion components that allow a subgingival implant to have the same contour and structure as a transgingival implant. To convert a subgingival implant, a tubular member having an outer counter the same as the gingival head section of the transgingival implant is non-rotationally attached to the hexagonal fitting on the upper end of the subgingival implant. The fastener holding the tubular member on the implant extends above the tubular component and usually contains a non-rotational fitting (e.g. a hexagon). To convert the transgingival implant, a single transition component is threaded into the bore of the transgingival implant. The upper part of the transition component has the same contour as the portion of the fastener (used with the tubular member) extending above the tubular member. Thus, these conversion components provide a precise configuration that is present on both a converted transgingival implant and a converted subgingival implant which allows both to use the same restoration components.

The inventive single-stage implant system further contemplates novel components to mate with the posts of the implants. The posts and abutments (hereinafter "posts" for convenience) on which artificial teeth are mounted generally extend supragingivally from a base at or beneath the gum surface to an end that may be narrower than the base. One inventive cap is hollow and open at least at its lower end so as to envelop the post in a generally telescopic manner when placed over the post. The end of the cap facing the base of the post is fitted with a rim enclosing an annular hollow space so as to snap over the periphery of the base when the cap encloses the post. When so fitted over the post, the cap covers the post and prevents the gum tissue from collapsing around the base of the post and top of the implant. It may also maintain an opening through the gum tissue for use by the restored tooth that is eventually mounted on the post. If it is desired for the cap to function as a temporary tooth, a suitable temporary cement can be used to fill the space between the cap and the post, in which event the hole in the top of the cap will serve as a vent for excess cement.

In another embodiment of the invention, the cap is open at its top and has perforations through its sides. When this embodiment is fitted over the post and covered with a tooth-shaped shell filled with a suitable dental plastic material that can be forced through the perforations into contact with the post and allowed to harden in a short time, a temporary tooth in the shape of the shell can be fashioned at chairside in the mouth of a patient, or on a model of the patient's case out of the patient's mouth. When the plastic material hardens, the shell can be removed, and this tooth can be cemented to the post to function as a temporary tooth which is cosmetically similar to adjacent teeth.

The above summary of the present invention is not intended to represent each embodiment, or every aspect, of the present invention. This is the purpose of the figures and the detailed description which follow.

BRIEF DESCRIPTION OF THE DRAWINGS

In the accompanying drawings:

FIG. 19 is a longitudinal section taken through the middle of a cap embodying the invention;

FIG. 20 is a bottom plan view of the cap of FIG. 19;

FIG. 21 is an enlarged view of the lower right-hand corner of the cap of FIG. 19;

FIGS. 23a–23c are a vertical section, a top perspective, and a bottom perspective view taken through the middle of the cap of FIG. 22;

DETAILED DESCRIPTION OF THE DRAWINGS

Figure 1C:
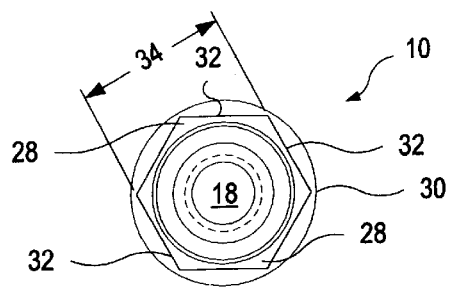
FIGS. 1a–1c are side, insertion end, and gingival end views of an implant according to the present invention.
Figure 1A:
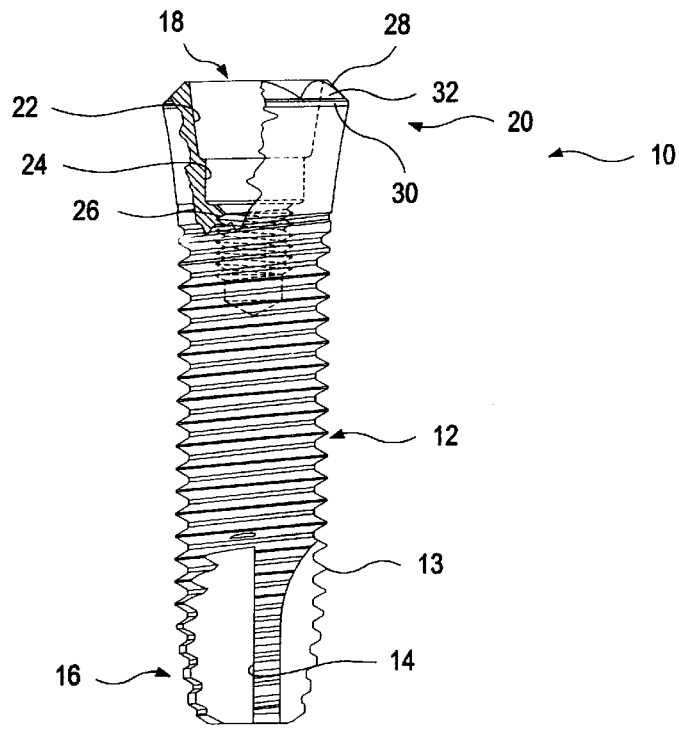
Figure 1B:
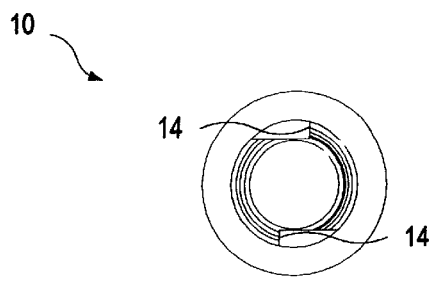

FIGS. 1a–1c illustrate an implant 10 having a main body 12 with a threaded outer surface 13. The threaded outer surface 13 includes a self-tapping region with incremental cutting edges 14 at an apical end 16 of the main body 12. These incremental cutting edges 14 are defined in detail in U.S. Pat. No. 5,727,943, entitled "Self-Tapping, Screw-Type Dental Implant" which is herein incorporated by reference in its entirety.

An axial opening 18 in a gingival end 20 of the main body 12 has three distinct zones proceeding from the uppermost edge of the gingival end 20 into the interior of the implant 10. An inwardly-tapering zone 22 is followed by a substantially cylindrical zone 24 which, in turn, is followed by an internally-threaded zone 26.

An outer surface 28 tapers downwardly from the uppermost edge of the gingival end 20 to a maximum diameter region 30. On the outer surface 28 between the uppermost edge of the implant 10 and the maximum diameter region 30 is a set of flat surfaces 32 shown here in a commonly-used hexagonal configuration. This set of flat surfaces 32 can be engageable with a tool that screws the implant 10 into the bone tissue. Alternatively, the set of flat surfaces 32 may be engaged by a carrier that is delivered with the implant 10 such that the clinician applies torque to the carrier which then is transferred into the implant 10 (see FIG. 10). The distance 34 between two parallel flat surfaces 32 can be made larger than the major diameter of the threads defining the threaded outer surface 13 of the main body 12 of the implant 10.

With regard to the details of the structure in the gingival end 20, each of the three zones 22, 24 and 26 of the opening 18 has a unique function. Each function is useful in connection with several different components of the system. These components will be discussed with reference to FIGS. 6–10.

Figure 2C:
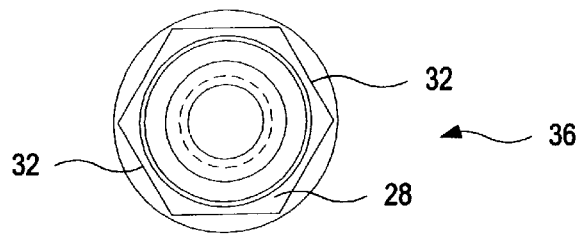
FIGS. 2a–2c are side, insertion end, and gingival end views of an implant.
Figure 2A:
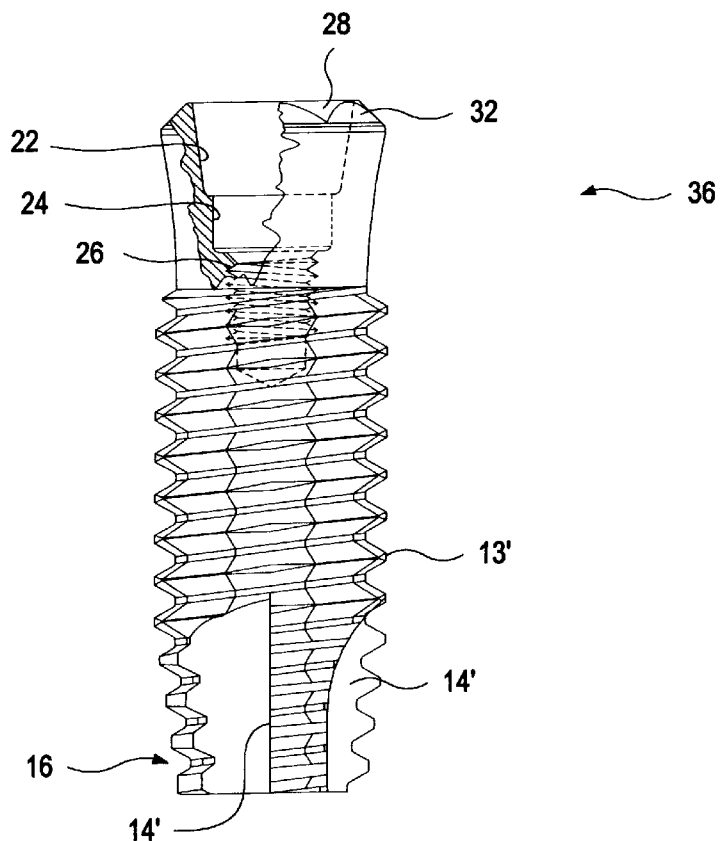
Figure 2B:
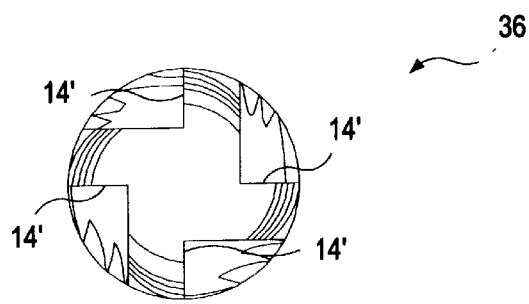

FIGS. 2a–2c disclose an implant 36 that differs from the implant 10 of FIG. 1 in the details of cutting edges 14' and the contours of the threads defining the threaded outer surface 13'. When viewed in cross-section, the threaded outer surface 13' is non-circular in the region of the threads and/or the troughs between the threads. This type of thread structure is defined in detail in U.S. application Ser. No. 08/782,056, filed Jan. 13, 1997, entitled "Reduced Friction, Screw-Type Dental Implant" which is herein incorporated by reference in its entirety. However, the zones 22, 24, and 26 of the opening 18 and the structure at the gingival end 20 are the same in the implant 36 as the implant 10 of FIGS. 1a–1c.

Figure 3:
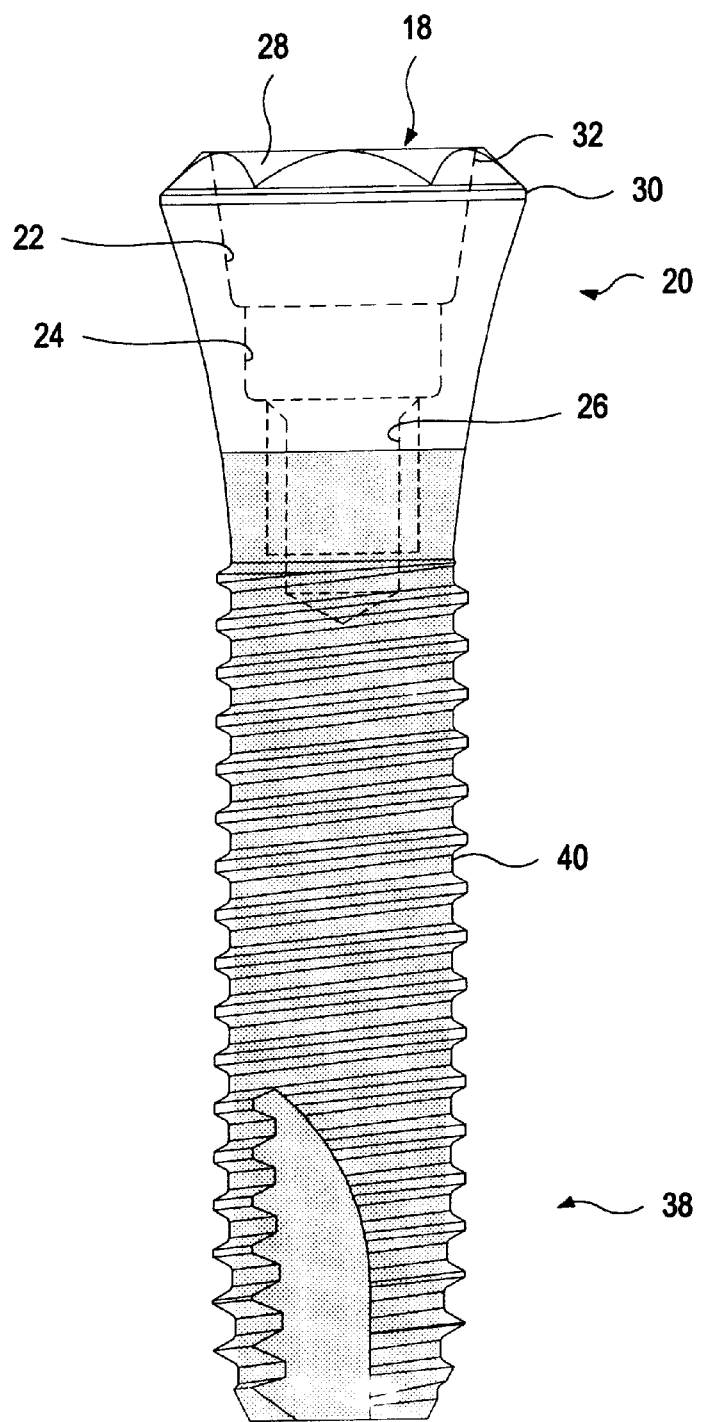
FIGS. 3 and 4 are side views of an implant with a roughened outer surface.

In FIG. 3, an implant 38 has a roughened outer threaded surface 40. The roughened outer threaded surface 40 may be produced through grit blasting or acid etching, or a combination of these two procedures. Exemplary processes of grit blasting and acid etching are described in U.S. Pat. Nos. 5,607,480 and 5,603,338 which are herein incorporated by reference in their entirety. The roughened outer threaded surface 40 enhances the osseointegration process. However, the gingival end 20 has a smooth outer surface such that it will not irritate the soft gingival tissue that contacts the gingival end 20.

Figure 4:
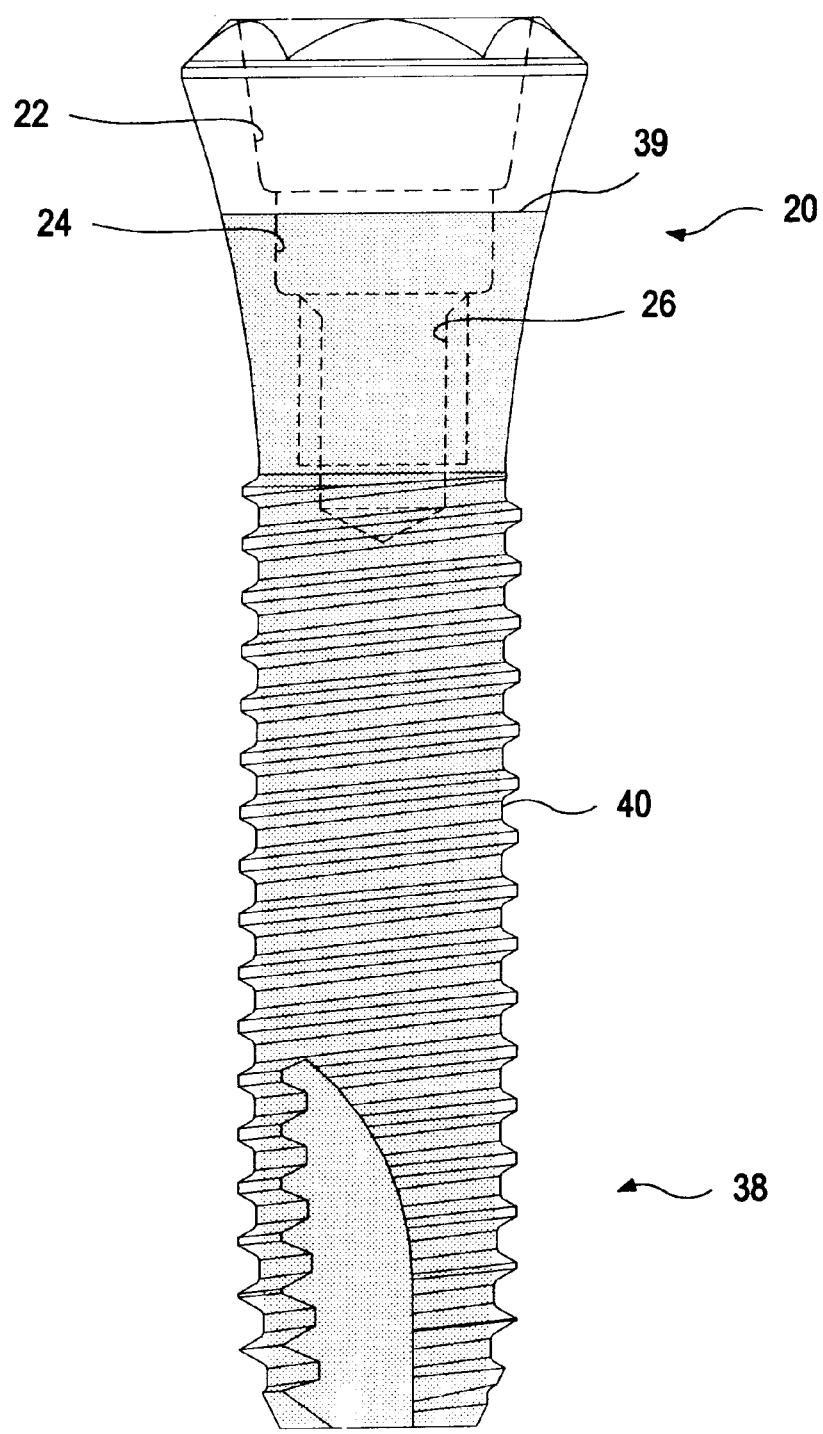

In FIG. 4, the implant 38 of FIG. 3 is illustrated having a roughened outer threaded surface 40 that extends into the gingival end 20. Thus, a transition line 39 between the roughened outer threaded surface 40 and the smooth surface at the gingival end 20 is located within the second zone 24. The positioning of the transition line 39 closer to the gingival end 20 may be useful in situations where more of the gingival end 20 is inserted into the bone.

Figure 5C:
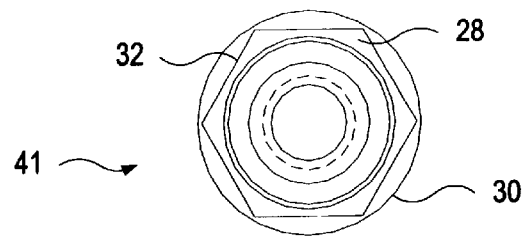
FIGS. 5a–5c are side, insertion end, and gingival end views of a wide-diameter implant.
Figure 5A:
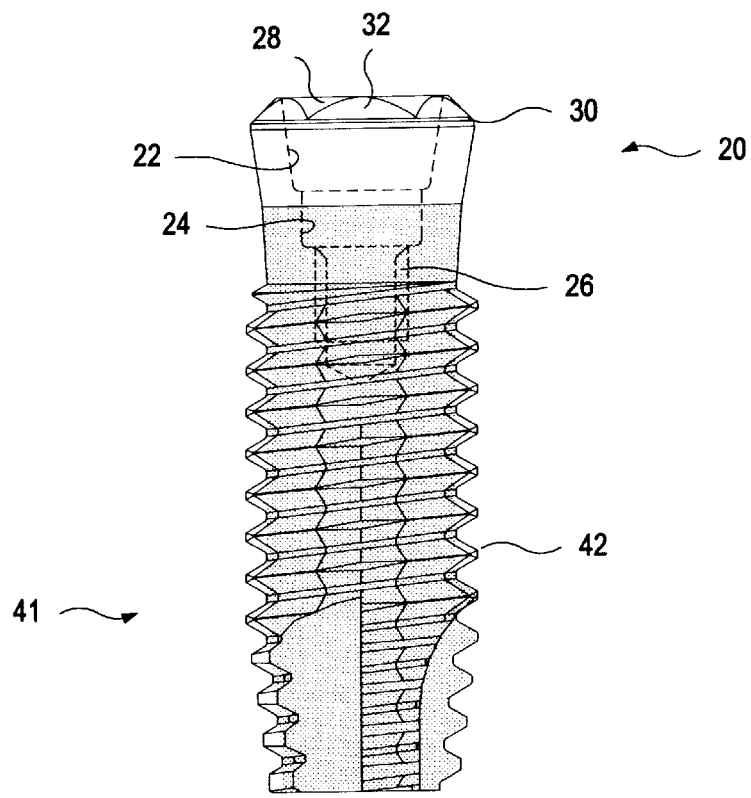
Figure 5B:
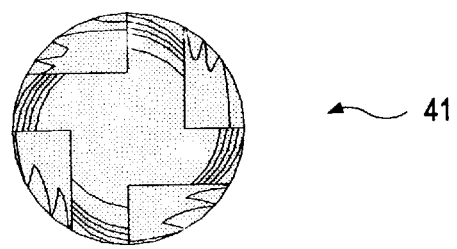
Figure 6D:
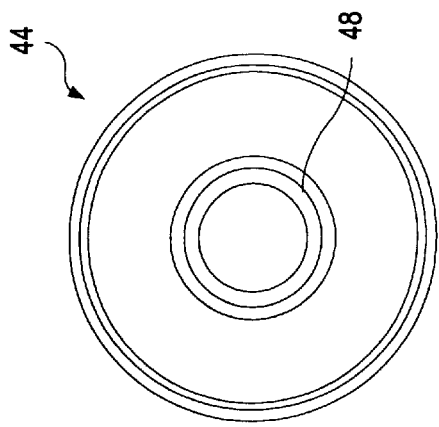
FIGS. 6a–6d are side, section, head end, and insertion end views of a cover screw.
Figure 6A:
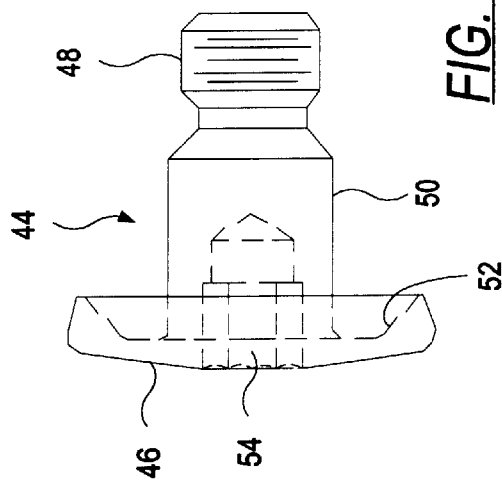
Figure 6B:
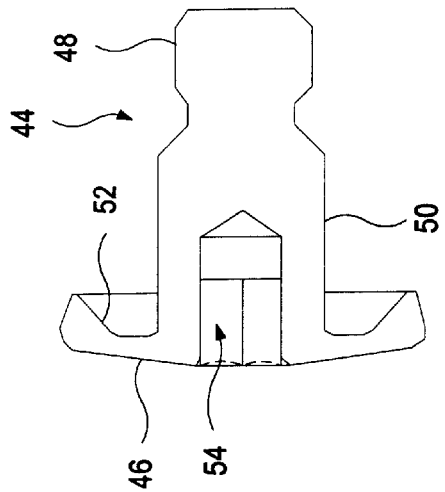
Figure 6C:
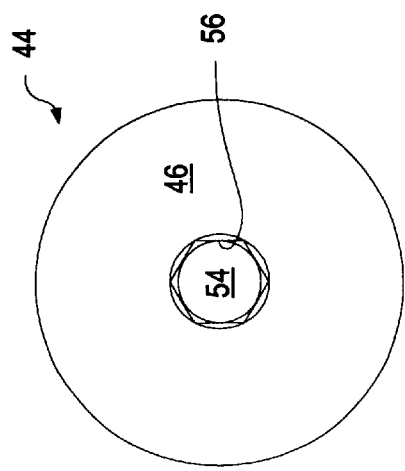
Figure 7D:
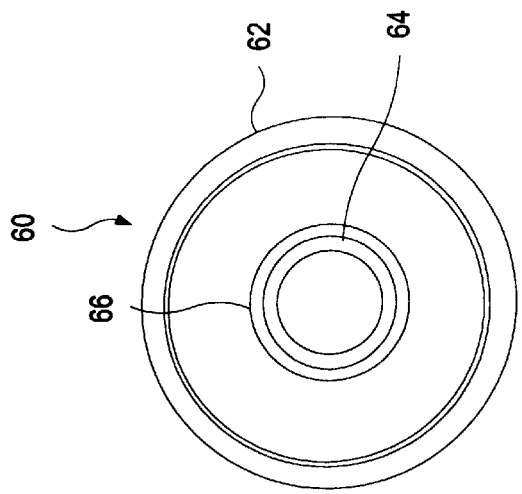
FIGS. 7a–7d are side, section, head end, and insertion end views of a cover screw.
Figure 7A:
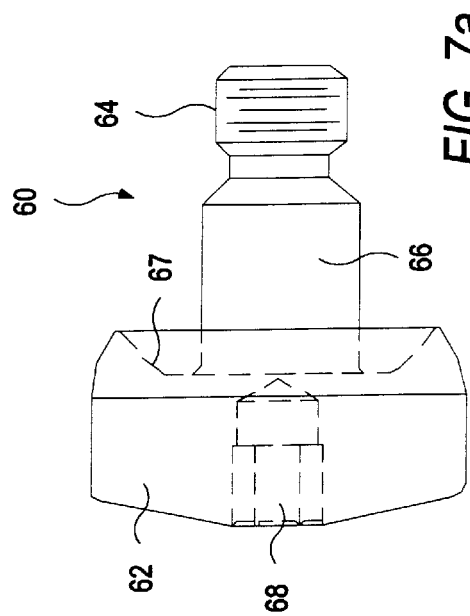
Figure 7B:
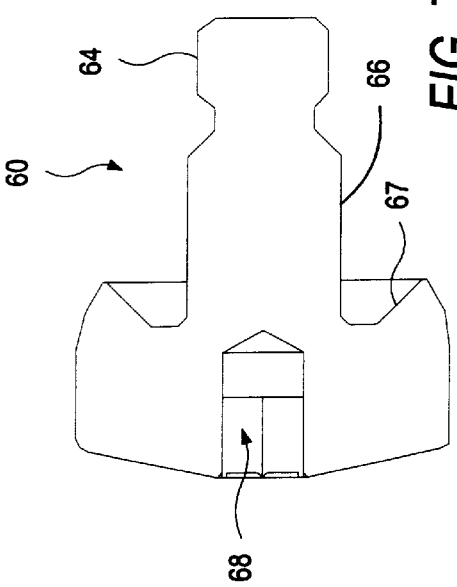
Figure 7C:
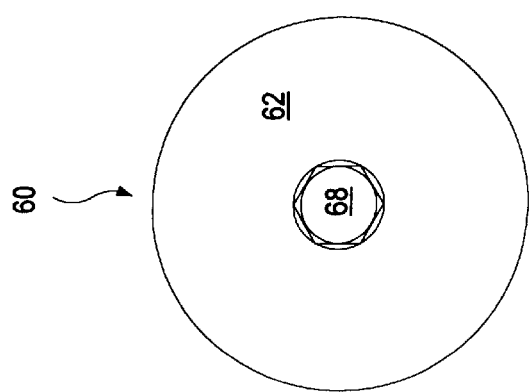

In FIGS. 5a–5c, an implant 41 having a wide diameter in the region of its roughed outer threaded surface 42 is illustrated. The diameter is in the range from about 4.5 mm to about 6.0 mm with the diameter of 5.0 mm being a fairly common dimension for a wide diameter implant. Such an implant 41 is useful to engage one or both cortical bones to provide enhanced stability, especially during the period of time after installation. The gingival end 20 again is structurally the same as the implants of FIGS. 1–4.

Several types of components are attachable to the implants of FIGS. 1–5. FIGS. 6–8 illustrate various types of cover screw that are inserted into the implant 10. Referring initially to FIGS. 6a–6d, a cover screw 44 has a head 46, an externally-threaded insertion end 48, and a cylindrical shaft 50 between the head 46 and the insertion end 48.

In use, the insertion end 48 of the cover screw 44 is threaded into the internally-threaded zone 26 of the opening 18 of the implant 10. The cylindrical shaft 50 fits within the cylindrical zone 24 of the opening 18 of the implants in FIGS. 1–5. The mating of the cylindrical zone 24 and cylindrical shaft 50 provide stability during insertion of the cover screw 44 into the opening 18. The head 46 has a reentrant under-surface 52 which covers the outer surface 28 and the flat surfaces 32 of the implant when the cover screw 44 is placed on the implant of FIGS. 1–5. The head 46 also has a bore 54 with flat surfaces 56 for engaging a tool, such as an Allen wrench, that turns the cover screw 44 into the internally-threaded zone 26 of the implant.

FIGS. 7a–7d illustrates a cover screw 60 having a head 62, a threaded insertion end 64, and cylindrical shaft 66 between the head 62 and the insertion end 64. The threaded insertion end 64 threadably engages the internally threaded zone 26 of the implants of FIGS. 1–5. The cylindrical shaft 66 resides within the cylindrical zone 24. The head 62 includes an undercut 67 that covers the outer surface 28 and the flat surfaces 32 of the implant. The head 62 also has a bore 68 with a region for engaging a tool that installs the cover screw 60 into the implant. The primary difference between the cover screw 60 and the cover screw 44 of FIG. 6 is that the head 62 of the cover screw 60 has an increased height such that it would extend further above the gingiva.

Figure 8C:
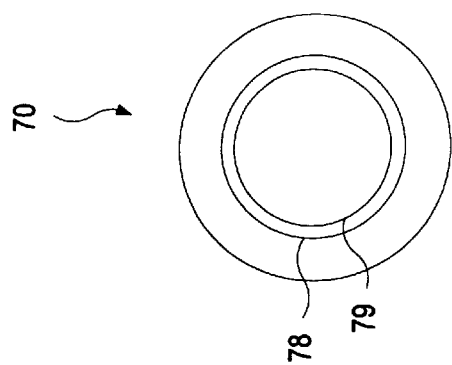
FIGS. 8a–8c are side, head-end, and insertion-end views of a cover screw.
Figure 8A:
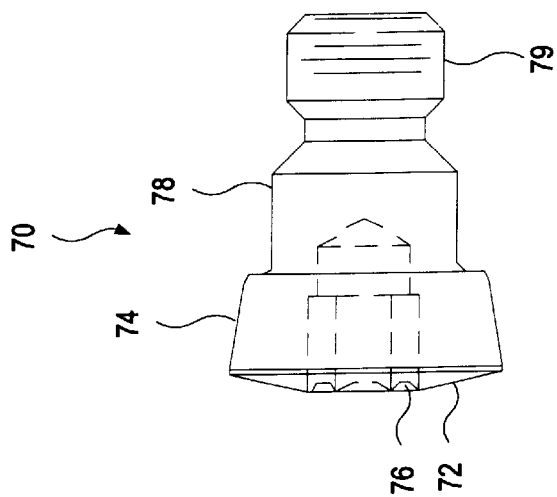
Figure 8B:
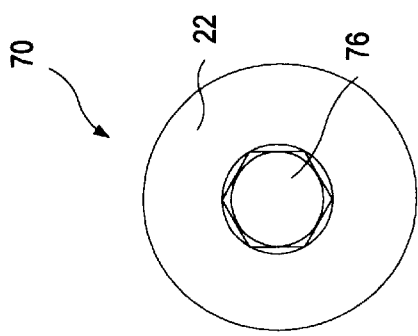

In FIGS. 8a–8c, a cover screw 70 has a head 72 with a tapering side-surface 74 for engaging the tapered zone 22 of the opening 18 of the implants of FIGS. 1–5. The upper surface of the head 72 would be approximately flush with the uppermost edge of the gingival end 20 of the implants. The tapering surfaces of the tapered zone 22 and the side-surface 74 are preferably tapered on the same angle suitably to provide a locking taper (e.g. about 18°) when those surfaces are engaged. A cylindrical shaft 78 is placed between the head 72 and a threaded insertion end 79.

The head 72 has a bore 76 with flat surfaces for engaging a wrench that turns the cover screw into the internally-threaded zone 26 of the opening 18. The cover screw 70 of FIG. 8 may be especially suitable for use with wide-diameter implants (e.g. FIG. 5), where the cover screw design of FIGS. 6 and 7 might be excessively bulky.

In FIGS. 9a–9d, an abutment post 80 includes four zones in a longitudinal sequence, namely, a supragingival zone 82, a locking-taper zone 84, a substantially cylindrical zone 86, and an externally-threaded zone 88. The last-mentioned three zones 84, 86 and 88 correspond, respectively, to the zones denominated 74, 78 and 79 in the cover screw 70 of FIG. 8. In use, the abutment post 80 is attached to one of the implants of FIGS. 1–5 by inserting the eternally-threaded zone 88 into the internally-threaded zone 26 of the opening 18 and rotating the post 80 until the tapered zones 84 and 22 engage and lock together. During the process of turning the post 80 into the implant, the cylindrical zones 24 and 86 provide axial stability that prohibits cross-threading the threaded surfaces of zones 88 and 26. The axial stability provides for true engagement of the tapering surfaces 84 and 22. The supragingival zone 82 has longitudinally-extending grooves 89 that are useful for engaging a tool to turn the post 80 into the implant. These grooves 84 are also helpful to hold a cemented prosthesis against rotation on the post 80.

To ensure that the tapering surfaces 84 and 22 do not resist in providing the required axial tension strain from the engagement of the threaded portions 88 and 26, the tapering surfaces 84 and 22 may be provided with a lubricant to reduce the friction between them. Biocompatible lubricants may be provided. Alternatively, the plating of one of the tapered surfaces, preferably the tapered surface 84 of the post 80, with gold may provide the necessary friction-reducing means. This type of friction-reducing plating is described in U.S. Provisional Application Serial Nos. 60/059,307 and 60/043,106, filed Sep. 17, 1997 and Apr. 17, 1997, respectively, and entitled "Dental Implant System having Improved Stability" and "Low Insertion Torque Screws for Use With Dental Implants", respectively, which are herein incorporated by reference in their entirety. Thus, the locking tapers may be lubricated through traditional biocompatible lubricants or metallic molecules which serves as a solid type of lubricant.

Figure 9C:
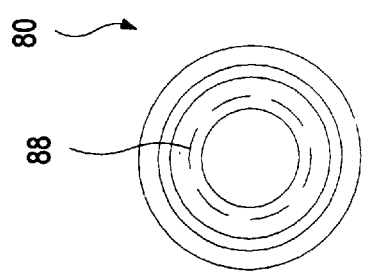
FIGS. 9a–9d are a side view, supragingival end view, insertion end view, and an assembly view of an abutment post for supporting a dental prosthesis.
Figure 9A:
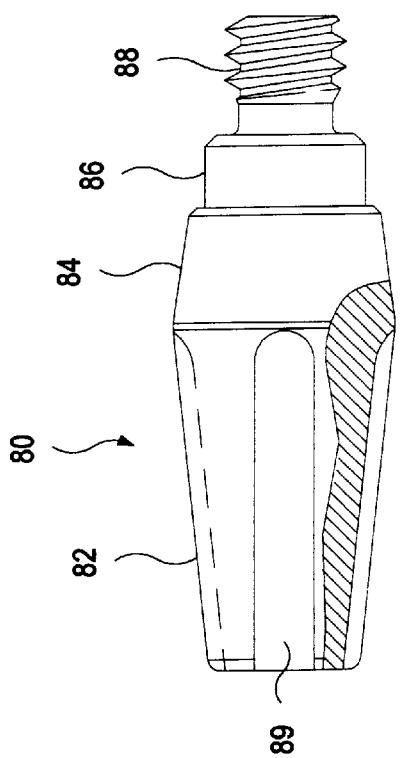
Figure 9B:
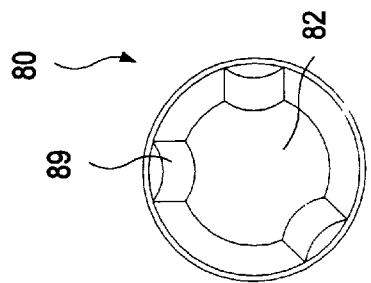
Figure 9D:
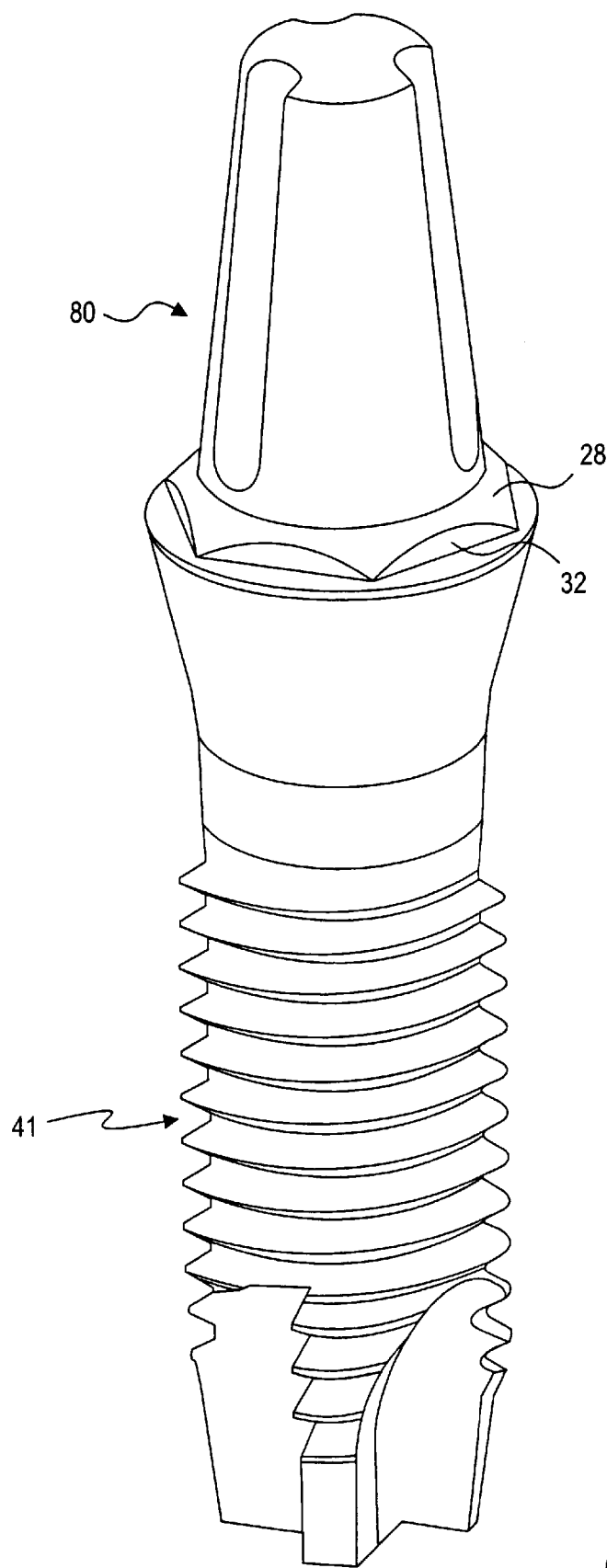

As shown in FIG. 9d, when the post 80 is assembled on an implant, such as implant 41 of FIG. 5, the flat surfaces 32 are outside the post 80. Thus, the flat surfaces 32 also serve the function of engaging a prosthesis against rotation on the implant, independent of any engagement between the prosthesis and the post 80.

As an alternative post configuration, the post may be made of two pieces, a tubular member to mate with the outer surface 28 and a threaded post that is inserted through the tubular member and holds the tubular member on the implant. Such a two-piece abutment system is disclosed in U.S. Ser. No. 08/729,869, filed Oct. 15, 1996, entitled "Two-Piece Dental Abutment," which is herein incorporated by reference in its entirety.

Figure 10:
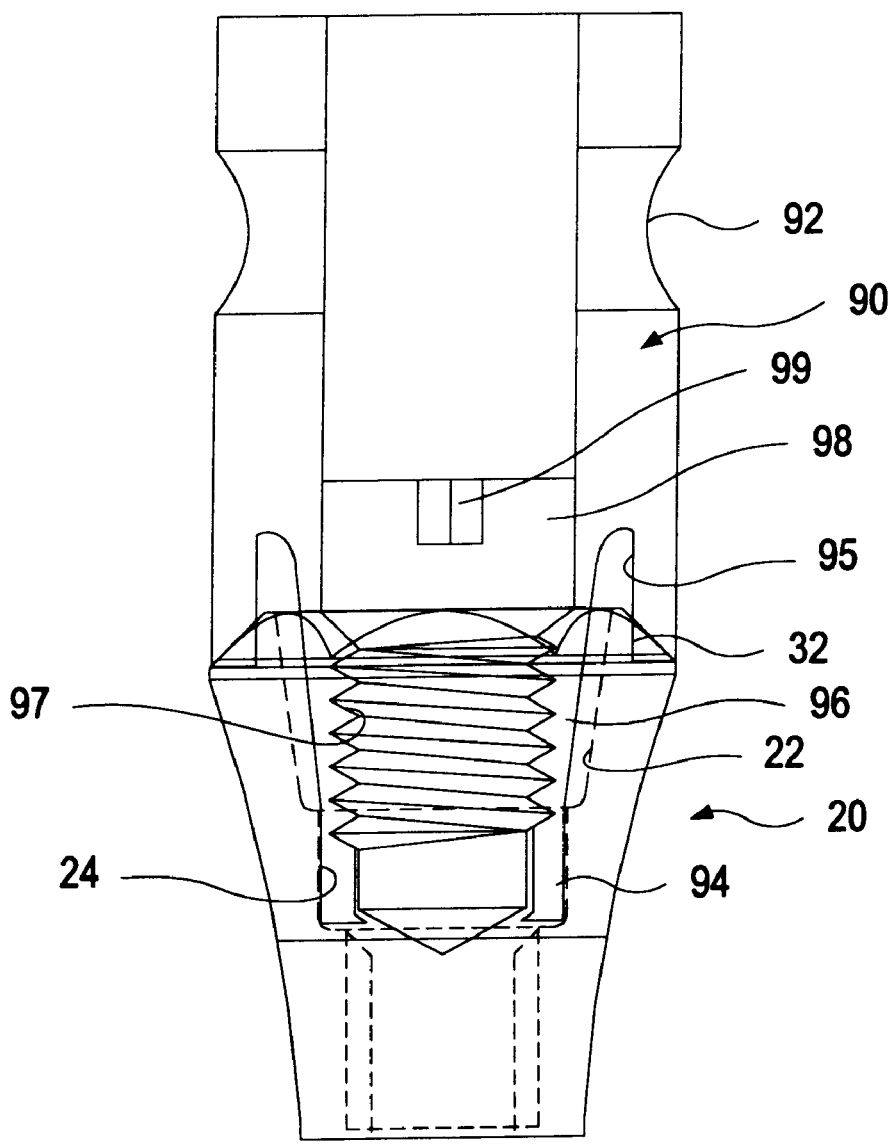
FIG. 10 is a side view of a gingival end of an implant with a carrier attached thereto.

In FIG. 10, a carrier for the implants of FIGS. 1–5 includes a main body 90 that has a structure 92 for engaging a driving tool that provides torque to the combination of the carrier and the implant. Although that structure 92 is illustrated on the exterior surfaces of the main body 90, that structure may be located on the interior surface of the main body 90 as well. The main body 90 includes an extending portion 94 that has at its lowermost portion a diameter that is narrow enough to be inserted into the cylindrical zone 24 of the gingival end 20 of the implant.

The main body 90 includes an overlapping region with an internal surface 95 that fits over the flat surfaces 32 of the gingival end 20. The internal surface 95 has the cross-sectional shape of a hexagon to mate with the hexagonal shape of the flat surfaces 32.

Between the overlapping region and the extending portion 94 is a tapered region 96 that fits the tapered zone 22 of the gingival end 20. However, the tapered region 96 does not need to engage the tapered zone 22. Although not shown, the extending portion 94 and the shank region 96 have an axially extending slot whose function is described below.

The extending portion 94 and shank portion have internal threads 97 that mate with screw 98 that is inserted into the bore of the main body 90. When the screw 98 is inserted into the internal threads 97, the extending portion 94 expands outwardly so as to become in tight frictional engagement with the cylindrical zone 24 of the implant. This process of affixing the carrier onto the implant is typically performed at the manufacturer's facility such that the carrier and the implant are delivered to the clinician as one unit. When the clinician uses the combination of the carrier and the implant, he or she places the apical end 16 of the implant 10 (see e.g. FIG. 1) into a bore in the jawbone. The clinician then uses a tool that engages the structure 92 on the main body 90, to turn the implant (with its self-tapping threads) into the bore. When the implant is inserted to the proper depth, the clinician then engages the non-circular bore 99 of the screw 98 with a tool and removes it from the implant. To ensure that the torque applied to the screw 98 during its removal does not rotate the entire implant, the direction of the thread of the screw 98 is chosen such that the applied torque would cause the implant to be further inserted into the bone. However, since the insertion of the implant would require more torque than the torque necessary to remove the screw 98, the implant remains motionless while the screw 98 is removed.

Figure 11C:
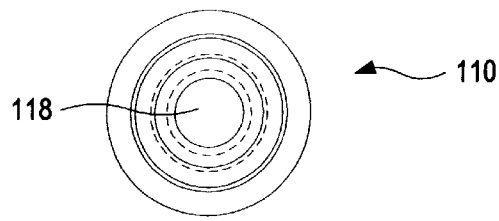
FIGS. 11a–11c are side, insertion end, and gingival end views of an implant.
Figure 11A:
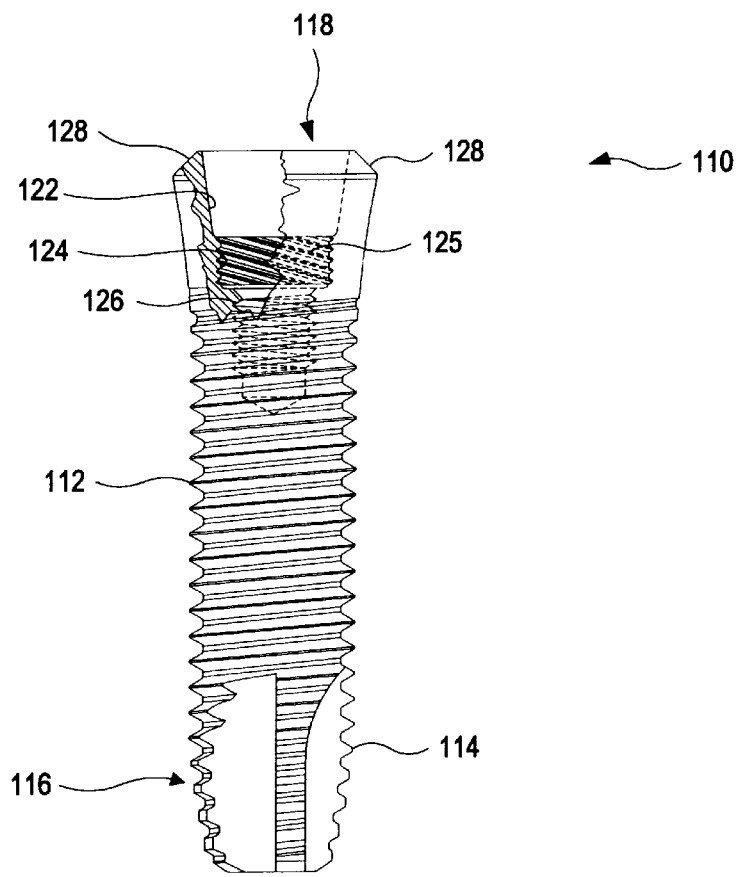
Figure 11B:
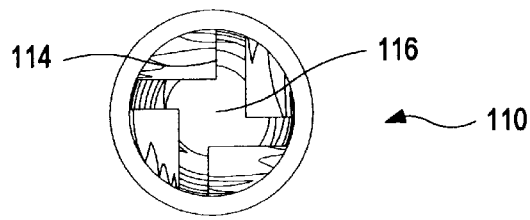

The implant 110 of FIGS. 11a–11c differ from implants of FIGS. 1–5 in that the implant 110 has a cylindrical zone 124 that is fitted with shallow helical grooves 125 in the surface of the wall defining the cylindrical zone 124. Thus, a portion of this wall defining the cylindrical zone 124 remains intact as it forms the lands between adjacent grooves 125. Furthermore, the implant 110 lacks the flat surfaces on its outer surface that form the hexagon on the gingival end as is shown in the implants of FIGS. 1–5. In other words, the outer surface 128 of the implant 110 is smooth. However, the remaining structures of implant 110 are the same as implant 10 of FIG. 1 and, thus, those remaining structures are now denoted by a 100-Series reference numeral.

Figure 12:
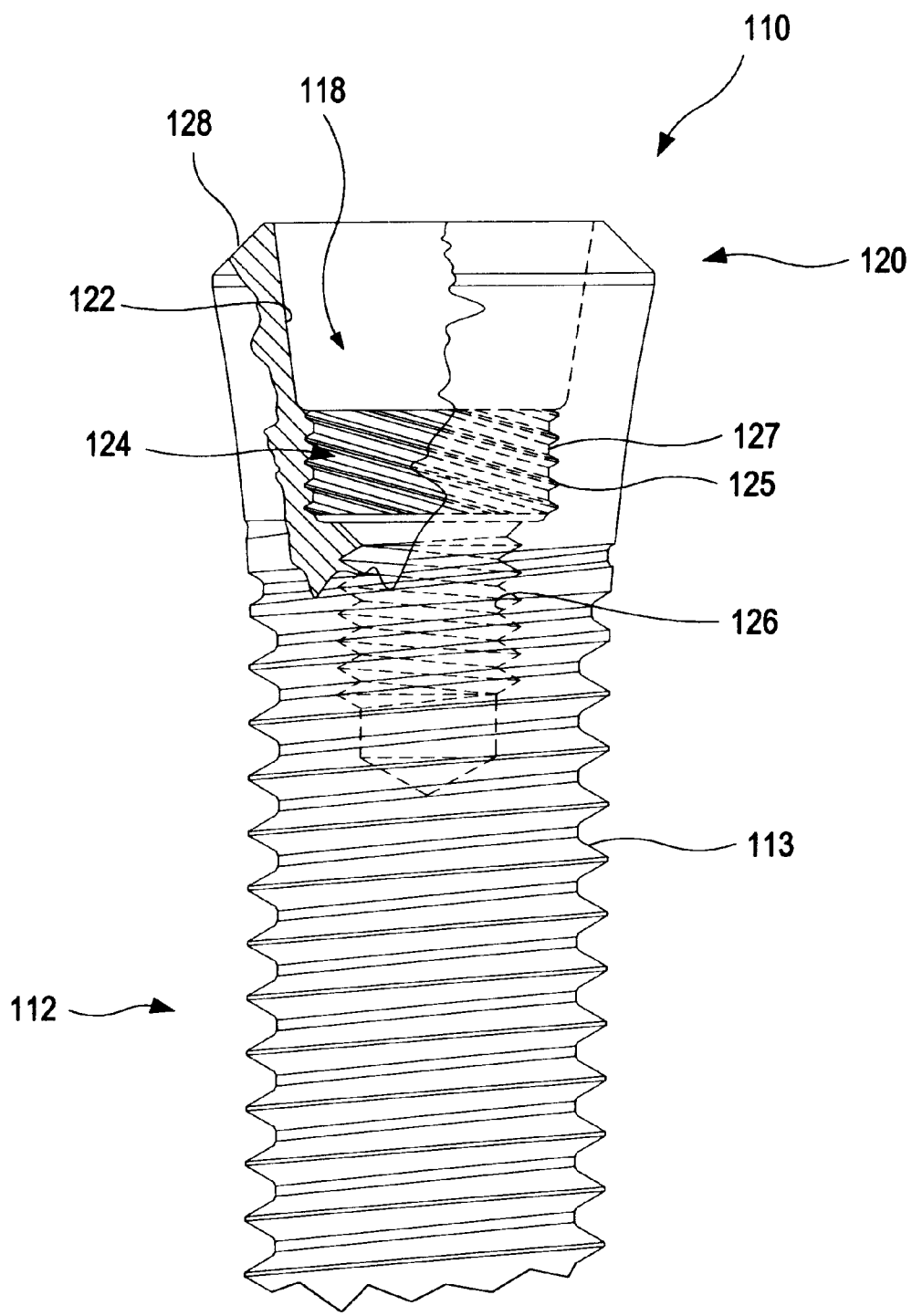
FIG. 12 is an enlarged view of the gingival end of FIG. 11.

Referring now to FIG. 12, the cylindrical zone 124 of the opening 118 is shown in detail. Four grooves 125 form a multi-lead thread having a relatively large pitch. The grooves 125 do not cut deeply into the cylinder wall so that they leave relatively wide lands 127 between adjacent grooves 125 thereby preserving the portion of the cylinder wall intact. In one practical embodiment of the implant 110, the axial length of the cylindrical zone 124 is a little more than 1 mm and the pitch of the threads formed by the grooves 125 about 1 mm. Thus, a single turn of a screw threadably mating with the grooves 125 serves to insert or remove that screw from the zone 124.

Even with the structure of the cylindrical zone 124 of FIGS. 11–12, the implant 110 can cooperate with the covers screws of FIGS. 6–8, and with the abutment post 80 of FIG. 9. Additionally, it serves functions related to the purposes of the implant mount and screw shown in FIGS. 13 and 14.

Figure 13C:
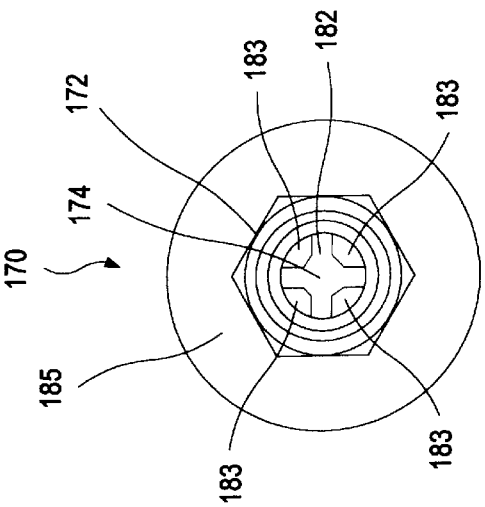
FIGS. 13a–13c are side, longitudinal section, and top end views of a mount body.
Figure 13B:
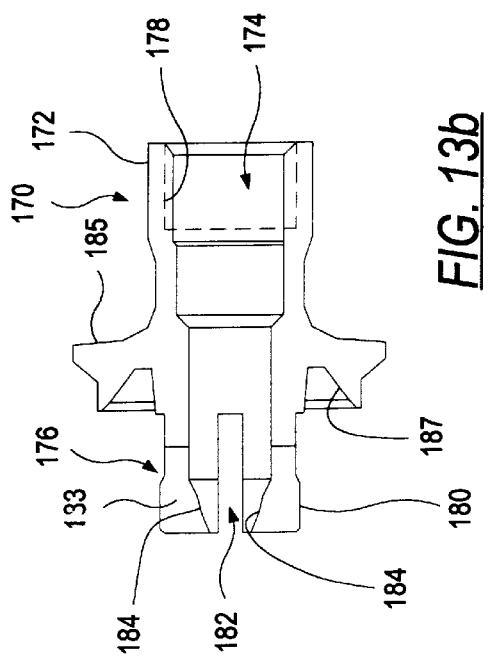
Figure 13A:
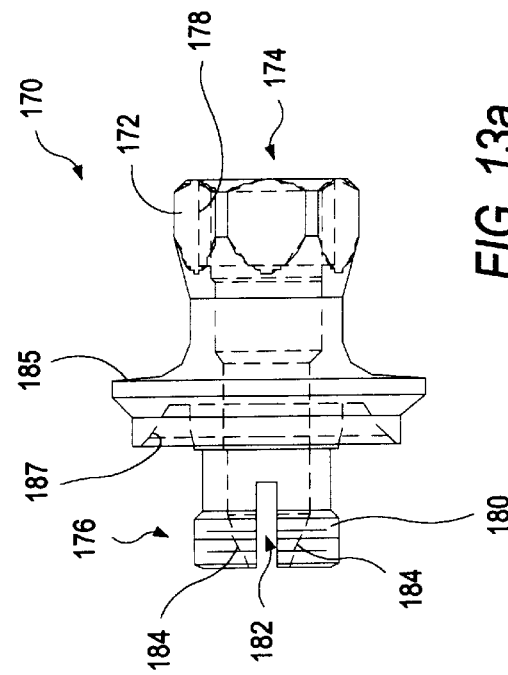

The implant mount 170, or carrier, shown in FIGS. 13a–13c has a head section 172 of non-round (here hexagonal) cross-section suitable for engaging with a socket wrench. The mount 170 has a through passage 174 extending from the head section 172 through a tail end 176. The through passage 174 has internal threads 178 in the head section 172. The tail end 176 has external threads 180 suitable for engaging the grooves 125 of the multi-lead thread in the cylinder zone 124 of the implant 110 of FIGS. 10–11. Longitudinally-directed slots 182 in the tail end 176 extend toward the head section 172. As seen best in FIG. 13C, four slots 182 are used in the illustrated embodiment, forming four fingers 183 in the tail-end 176. These slots 182 may all be the same length, or they may have different lengths. In one embodiment, one pair of opposing slots are longer than the intervening pair. Immediately inside the tail end 176, the passage 174 is partially obstructed with wedge blocks 184, one of which is attached to each finger 183.

Between its ends, the mount 170 has a radially-extending flange 185 similar to the head 46 of the cover screws of FIG. 6 & 7. The flange 185 includes a reentrant under-surface 187 that engages the outer surface 128 of the gingival end 120.

Figure 14B:
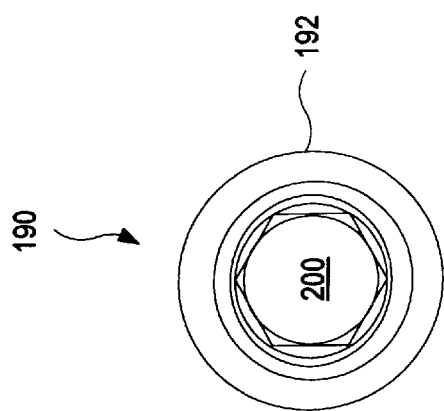
FIGS. 14a–14b are a mount screw and a head-end view for use with the mount body of FIG. 13.
Figure 14A:
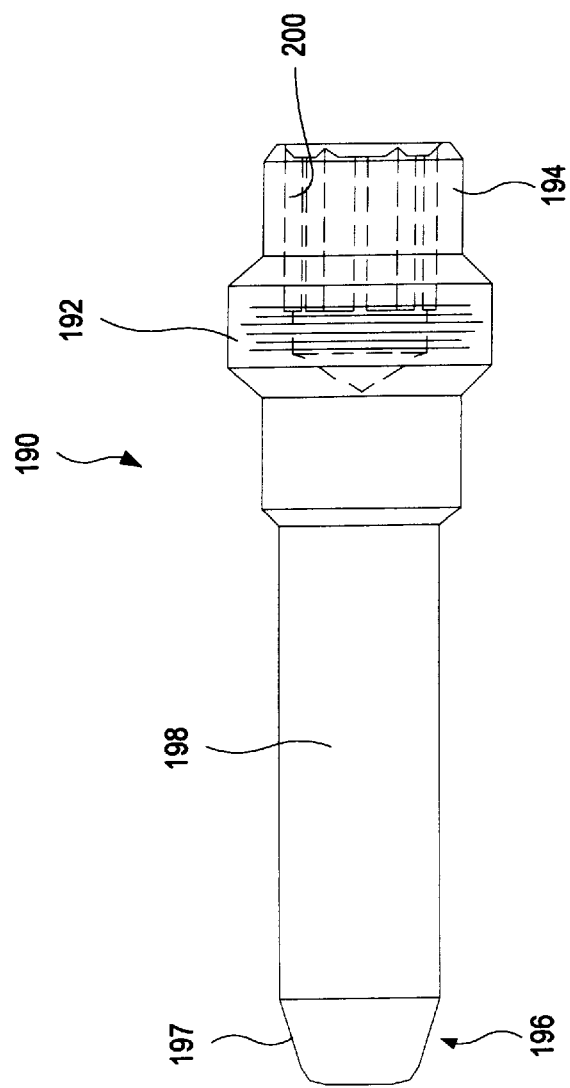

The mount screw 190 of FIG. 14 has an externally-threaded section 192 between its head end 194 and its tail end 196. A cylindrical shaft 198 extends between the threaded section 192 and the tail end 196 suitably dimensioned for fitting within the passage 174 of the implant mount 170. At the tail end 196, the shaft 198 has a tapered end-section 197 for engaging between the wedge blocks 184 of the implant mount 170. In its head end 194, the screw 190 has a non-round (here shown as hexagonal) socket 200 for engaging a wrench, such as an Allen wrench.

In use, the implant mount 170 of FIG. 13 is inserted through the implant passage 118 and threaded via the threads 180 at its tail end 176 into the threaded cylindrical zone 124 of the implant 110. In a preferred embodiment, approximately one turn is required to seat the flange 185 of the implant mount 170 over the outer surface 128 of the implant 110 using a torque of about 10 N-cm. The mount screw 190 is then inserted through the passage 174 of the implant mount 170 and its threaded section 192 is engaged in the internal threads 178 in the head section 172 of the mount 170. A suitable wrench engaged in the socket 200 is useful to drive the mount screw 170 into and between the wedge blocks 184 and thereby apply a radially-directed force to spread the tail end 176 within the cylindrical zone 124 using a torque of about 15 N-cm.

The implant 110 of FIG. 11 with the implant mount 170 and screw 190 (FIGS. 13 and 14) installed as herein described are carried to the site in the mouth of the patient. The implant 110 is installed in the prepared site with a torque required to overcome the cutting of the bone at the self-tapping region. Such torque is generally less than about 40 N-cm. Tests applying torque forces in excess of 100 N-cm have shown that the fingers 184 may be expected to break when the torque exceeds about 120 N-cm which is a far greater torque than would be encountered in a real-life situation.

After the implant 110 has been installed in the patient's bone, the mount 170 is easily removed by loosening the screw 190 and turning the mount 170 in reverse by approximately one turn to release it from the implant 110. The invention also contemplates an embodiment where the screw 190 is held captive in the passage 174 of the mount 170 such that both pieces remain together during their removal from the implant.

With regard to the conversion between subgingival and transgingival implants, it is highly desirable for successful dental restoration that the components of a restoration system be precisely dimensioned and that dimensional precision be maintained at every stage in the process of constructing the restoration. For example, implants of the subgingival style are commonly fitted at their occlusal ends with an anti-rotational connecting element for coupling a transgingival component to the implant in a manner that prevents the component from rotating on the implant, around the axis of the implant. These anti-rotational connection elements usually take a hexagonal form, although octagonal forms are also in use. Because of manufacturing tolerance limitations, it is difficult to make hexagonal (for example) posts and sockets that will fit together so tightly that they will not allow some little amount of relative rotation between the connected implant and component. The degree of tightness required to eliminate all relative rotation would make connecting and disconnecting these two parts in the mouth of a patient so difficult that the patient would be unacceptably uncomfortable. A solution to this problem is described in the assignee's copending U.S. patent application Ser. No. 08/451,083, filed May 25, 1995, for "Anti-rotational Connecting Mechanism," now U.S. Pat. No. 5,725,375.

Experience has shown that available transition components tend to leave a small gap extending part-way around the periphery of the implant surface. This is believed to be due, at least in part, to the difficulty of accurately attaching restoration components to the transition component. This in turn makes it difficult to achieve and maintain precise axial alignment of the implant, the transition component and the restoration component. Accordingly, in addition to the inventive transgingival style of implant, the present invention addresses the alignment, tolerance, and gap problems as will be shown in FIGS. 15 and 16.

Figures 15, 16:
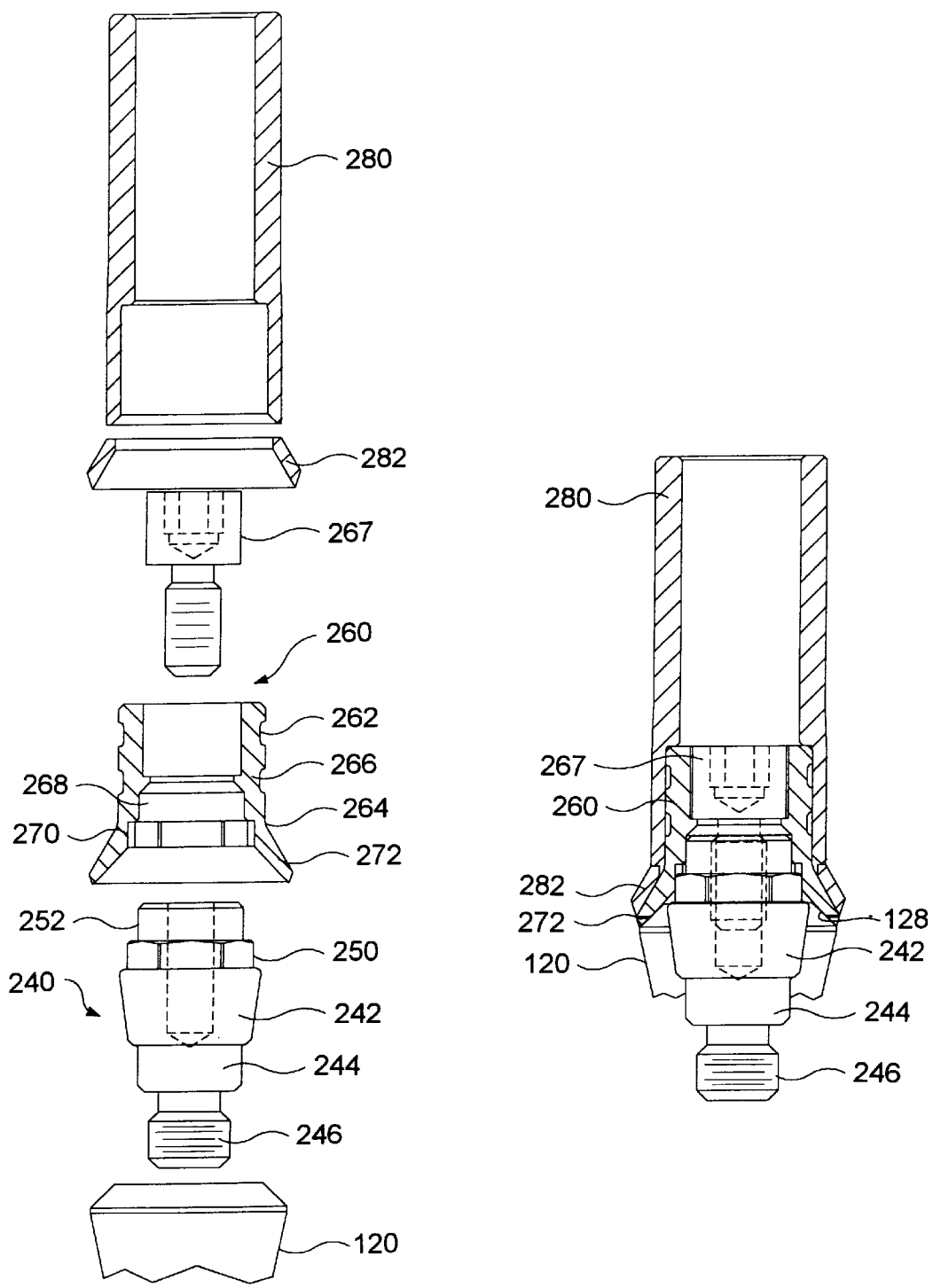
FIG. 15 is an exploded side elevation, partially in section, view of a transition component and associated components for use with a transgingival-style dental implant.
FIG. 16 shows the components of FIG. 15 assembled.

FIGS. 15 and 16 relate to conversion components for converting between a subgingival and transgingival implant. A transition component 240 has a lower section designed to fit into the implant 110 of FIGS. 11–12. This lower section includes a tapered zone 242, an intermediate zone 244 and an externally threaded zone 246 designed to fit in the corresponding zones 122, 124, and 126 of the implant bore 118. Specifically, the threaded zone 246 screws into the innermost zone 126 of the implant, the intermediate zone 244 mates with the intermediate zone 124 of the bore 118, and the tapered zone 242 seats in the outermost zone 122 of the implant bore 118. A locking taper is formed by the engaging side walls of the zones 122 and 242, and thus only a short thread section 246 is needed on the distal end of the transition component.

The transition component 240 also has an upper section that extends beyond the occlusal end of the implant. This upper section includes a hexagonal anti-rotation zone 250 and a locator zone 252, extending in sequence supragingivally from the implant when the transition component 240 is installed in the bore 118. The axial length of the locator zone 252 is preferably larger than the axial length of the anti-rotation zone 250. The locator zone 252 is preferably round in cross-section, and smaller in cross-sectional size than, the anti-rotation zone 250.

A hollow abutment 260, which performs the function of a non-rotating cylinder used to support an artificial tooth, fits over the upper section of the transition component 240 and the occlusal surface of the implant 110. The inside surface of the abutment 260 includes an upper section 262 and a lower section 264 separated by a flange 266. The upper section 262 receives the head of a retainer screw 267, with the screw head resting on the shoulder formed by the upper surface of the flange 266. The lower section 264 includes a locator zone 268 above the usual hexagonal socket 270, and a flared skirt 272 extends outwardly and downwardly from the bottom edge of the socket 270 to the bottom periphery of the abutment. The inside surface of the skirt 270 preferably flares on an angle (measured from the longitudinal axis through the implant and attached components) that is a little smaller than the slope angle of the outer surface 128 of the implant 110, so that the initial contact between these two surfaces occurs at the bottom edge of the skirt 272.

When the abutment 260 is fitted to the transition component 240, the locator zone 268 of the abutment makes first contact with the locator zone 252 and serves to align the abutment axially with the transition component. Because the two mating locator zones 252 and 268 are both cylindrical and very close to the same size, the abutment 260 can be turned around the common axis until the anti-rotation zones 250 and 270 are in register. The abutment 260 can then be seated accurately on the transition component 240, and the retainer screw 267 can be screwed into the bore 254 and tightened to seat the skirt 272 on the outer surface 128 of the implant 110.

Because the mating locator zones 268 and 272 guide and align the abutment 260 as it is fitted over the transition component 240, the abutment 260 is accurately seated on both the transition component 240 and the outer surface 128 of the implant 110, thereby avoiding any microgaps at the interface between the abutment and the implant. As described above, precise alignment is further facilitated by the fact that the outer periphery of the skirt 272 makes first contact with the outer surface 128 of the implant 110, and further tightening of the screw 267 increases the annular area of that contact.

The tube 280 shown in FIGS. 15 and 16 is a known component used to make an artificial tooth using the lost-wax process. The tube 280, which is typically made of a material that is burned away in the course of the lost-wax process, fits over the abutment 260 down to the skirt 272. A waxing sleeve 282 is provided to cover the skirt.

Figures 17, 18:
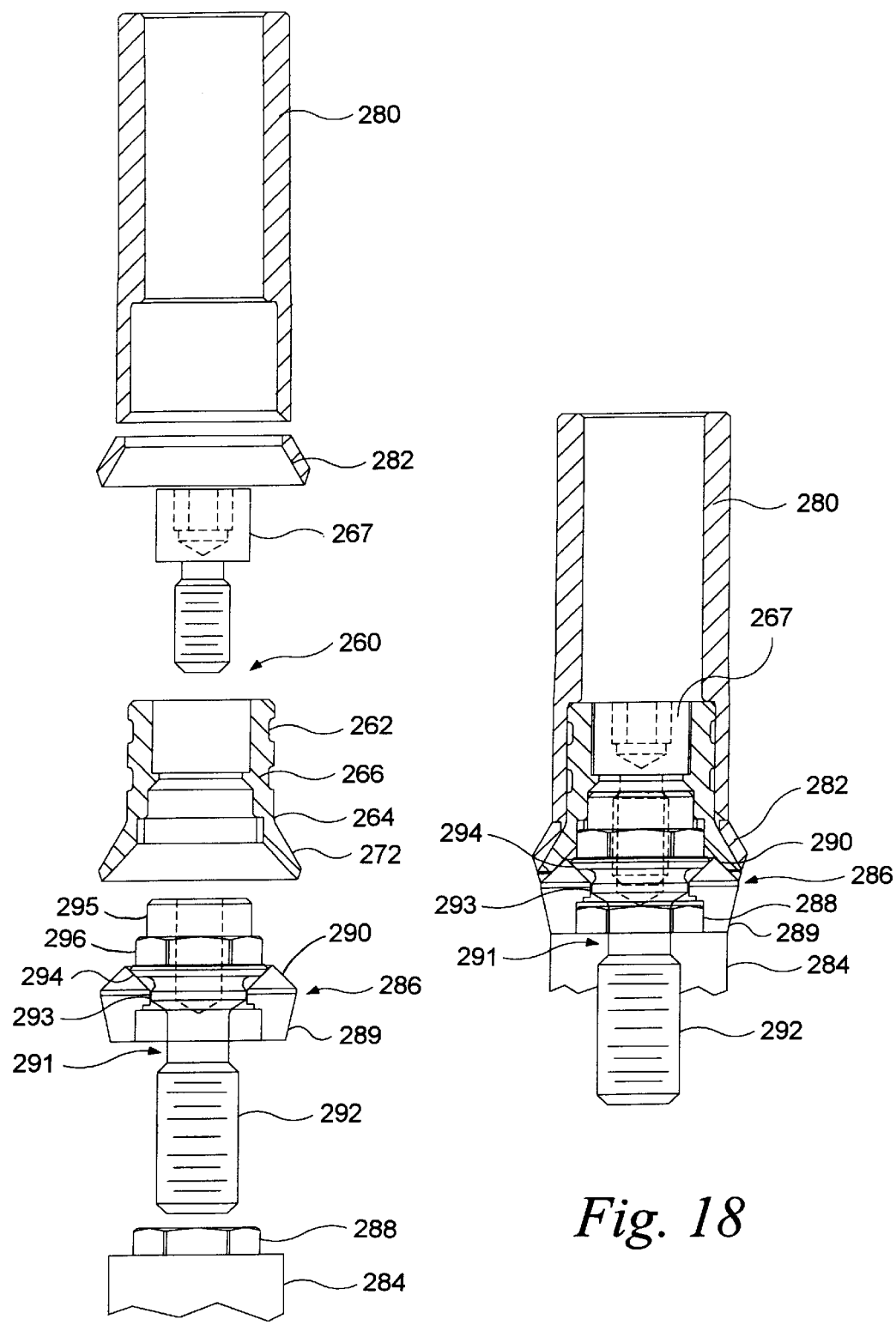
FIG. 17 is an exploded side elevation, partially in section, of a transition component and associated components for use with a subgingival-style implant.
FIG. 18 shows the components of FIG. 17 assembled.

The invention can be adapted to modification of a subgingival-style implant 284, as is shown in FIGS. 17 and 18, where parts common with FIGS. 15 and 16 bear the same reference characters. The subgingival-type dental implant 284 is indicated in part under an abutment ring 286 fitted non-rotationally to the anti-rotation (e.g., hexagonal) fitting 288 of the implant 284. This abutment ring 286 has an exterior side surface 289 that mimics the side surface of the transgingival section 120 of the transgingival implant 110 shown in FIGS. 11–12, and a sloping top surface 290 which mimics the sloping outer surface 128 of the transgingival implant 110.

An abutment screw 291 attaches the abutment ring 286 to the implant 284. This screw 291 has a threaded stem 292 which engages the usual threaded bore of the implant 284. Above the stem 292, cylindrical and tapered head sections 293 and 294 engage corresponding interior surfaces of the abutment ring 286. The portion of the screw head that projects above the abutment ring 286 is identical to the upper section of the transition component 240 described above. In other words, the head of the screw 291 includes a locater region 295 and an anti-rotation 296 (e.g. hexagonal boss) that are similar to locater zone 252 and anti-rotation zone 250 of the transition component 240. All the other parts shown in FIGS. 17 and 18 are the same as the corresponding parts in FIGS. 15 and 16. Thus, the abutment 260 and the tube 280 can be used with the subgingival implant 284 after it has been fitted with ring 286.

FIGS. 19–25 relate to caps which engage the post of a transgingival implant. In the first embodiment of the invention shown in FIGS. 19–21, a cap 310 has a generally cylindrical-shaped outer sidewall 312 and a tapered inner sidewall 314. This cap 310 has an open bottom 316 bounded by a rim 318 enclosing an annular channel 320. The outer sidewall 310 turns inward at the bottom 311 toward the rim 318. At the top 322 the cap has a dome-shaped top wall 324 with a hole 326 through it. The cap is preferably made of a resilient polymeric material that retains its shape, such as "Delrin."

Figures 22A, 22B, 22C:
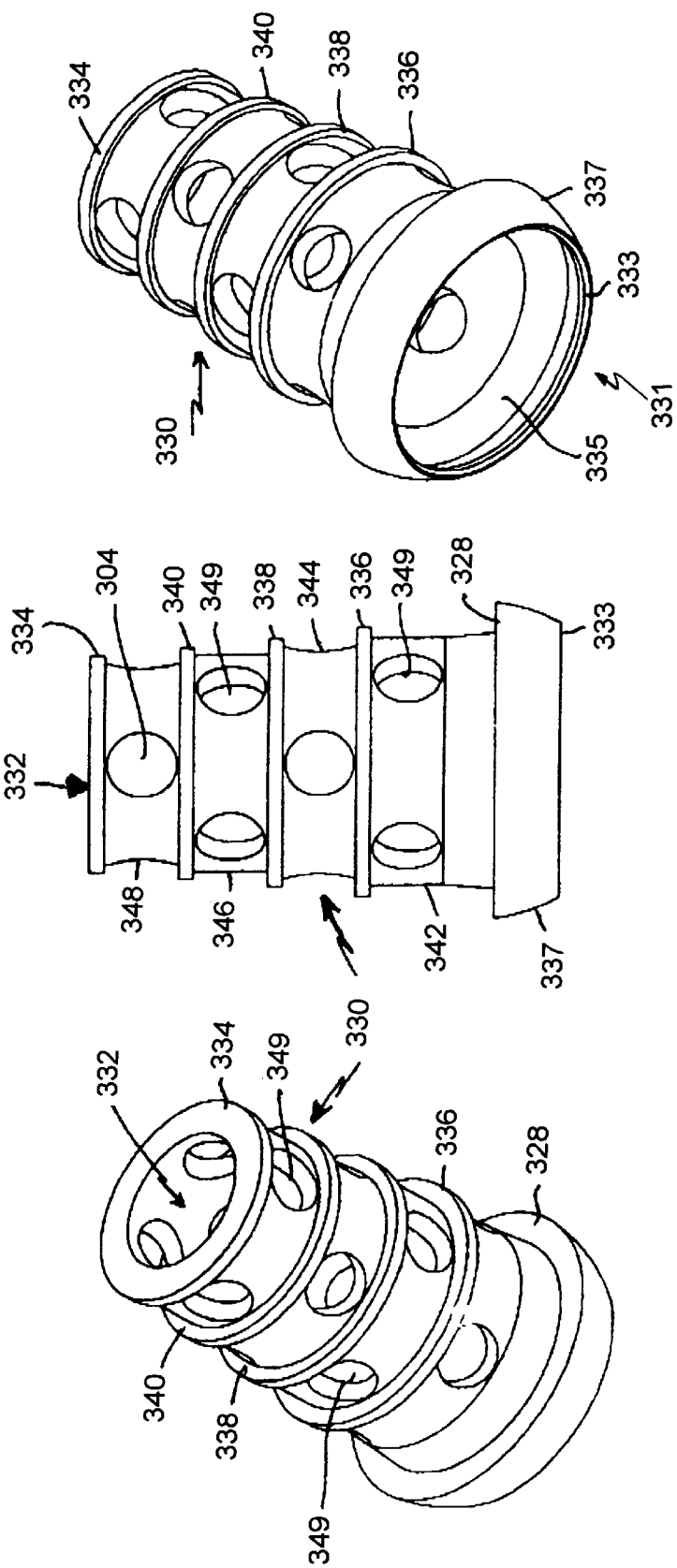
FIGS. 22a–22c are a side elevation, a top perspective, and a bottom perspective view of a modified cap embodying the invention.
Figure 24:
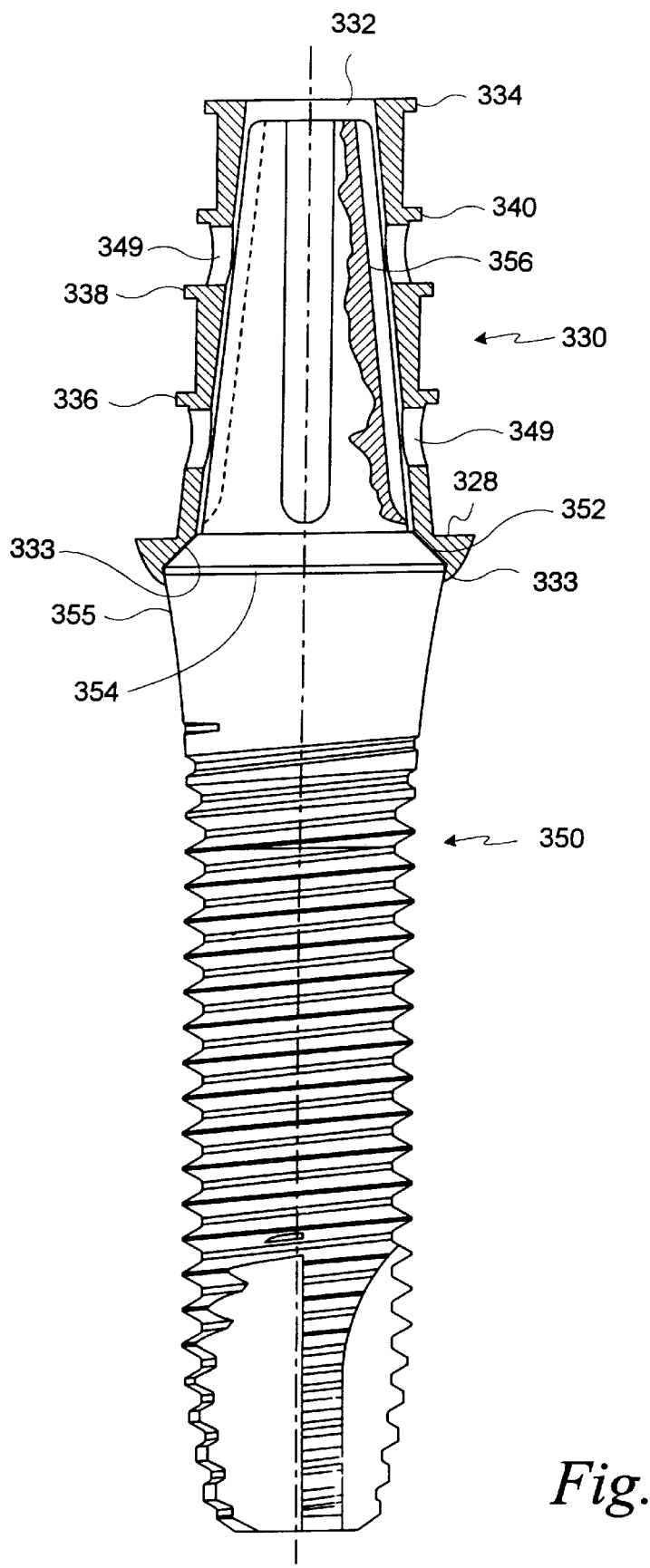
FIG. 24 is a side elevation, partially in section, of an implant system using the cap of FIGS. 22 and 23.

In a second embodiment of the cap invention shown in FIGS. 22–24, a cap 330 has an open bottom 331 bounded by a rim 333 enclosing an annular channel 335 like the same parts of the cap 310 in FIGS. 19–21. The top 332 of the cap 330 is open and surrounded by an annular rim 334. The inwardly-tapering bottom portion 337 of the sidewall has an upwardly-facing annular shoulder 328 at its upper end. Between this shoulder 328 and the top rim 334 are several additional rims 336, 338 and 340, which decrease progressively in diameter, as shown, from the shoulder 328 to the top rim 334. The shoulder 328 has the largest outer diameter, and the top rim 334 has the smallest outer diameter. A series of generally tubular sidewall sections 342, 344, 346 and 348 are fixed, respectively, between the shoulder 328 and the adjacent rim 336, then rim 336 and rim 338, then rim 338 and rim 340, and finally rim 340 and rim 334. The diameters of these sidewall sections decrease progressively from the shoulder 328 to the top 332 of the cap 330, so that the overall shape of the cap 330 is tapered in diameter from the lower opening 316 to the upper opening 332. Each sidewall section has perforations 349 through it.

The caps 310 and 330 of the invention are fitted to the previously-described implants of FIGS. 1–5, 11–12, and 15–18, which will be generically called dental implant 350, by forcing the rims 318 and 333 over the peripheral surface 354 at the bottom of an expanding sloping surface 352 at the top of the implant 350. The annular channels 320 and 335 have a shape complementary to that of the implant 350 so the upper portions of the channels 320 and 335 make contact with the sloping surface 352, while the lower portions of the channels 320 and 335 fit against the upper portion of an inwardly tapering surface 355 directly beneath the rim 354. To enable this lowermost portion of the cap to pass the rim 354 of the implant, the caps are preferably made of a resilient material so that downward pressure urging the lower rims of the cap 310 and 330 against the sloping implant surface 352 cams the rim 318 outwardly, thereby temporarily expanding the diameter of the bottom opening of the cap 330 until the rim 318 clears the implant rim 354. The resilience of the cap 330 then causes the rim 318 to snap back to its original diameter, against the inwardly tapering surface 355 beneath the rim 354. It will be appreciated that this same type of "snap action" may be used to hold the cap in virtually any undercut surface configuration near the top of an implant. As can be seen in FIG. 24, in its final installed position the cap 330 surrounds a post 356 that is in place on the implant 350.

In an alternative embodiment, the rims 318 and 333 can have a cylindrical internal lower configuration instead of the conical internal configuration. In this embodiment, the rims 318 and 333 of the caps 310 and 330 would engage the implant 350 along the upper sloping surface 352 and the small cylindrical band of the implant (at its widest diameter) just above the inwardly tapering surface 355. This band is usually about 0.004 in to 0.010 inch in height, although it could be made larger. Thus, the rims 318 and 333 of the caps 310 and 330 will have an internal cylindrical section with a similar length to engage the cylindrical band on the implant. Alternatively, the internal cylindrical section may be longer such that it extends below the cylindrical band on the implant 350 but does not engage the inwardly tapering surface 355 of the implant 350.

The cap 310 can be used by itself as a temporary tooth. The clinician applies a cement to the inside surface of the cap 310 and places it on the post. The excess cement then can vacate the cavity under the cap 310 through the hole 326. Because the cap 310 by itself serves as a temporary tooth and is made of relatively inexpensive plastic materials, the invention contemplates producing the cap in various sizes and shapes to generally mimic the outer contours of natural teeth. Thus, the clinician would select the size and shape that would best correspond to the conditions in the patient's mouth. Alternatively, the cap 310 could be modified by the clinician to produce a more esthetically pleasing contour. Furthermore, cap 310 can be simply used without cement for a short time (less than two days for example) to get the patient from the periodontist to the restorative dentist.

Also, the cap 310 can form the gingiva at its bottom 311. While in some instances a clinician will place the implant 350 such that its upper sloping surface 352 is at or above the outer gingival surface, some clinicians may place the implant 350 such that its upper sloping surface 352 is well below the gingival surface. Thus, the cap 310 may engage and form the gingiva for 2 mm to 3 mm above its lowermost surface.

Because the cap 310 will form a ring-shaped cavity in the gingiva adjacent to and around the inwardly tapering surface 355, the cap 310 is useful prior to taking an impression because it is beneficial to slightly move the gingival tissue away from the implant 350 before the impression process. Thus, the impression material can flow into this ring-shaped cavity to obtain a better impression of the region along the inwardly tapering surface 355 of the implant 350. While this process of displacing the gingival tissue occurs after the cap 310 has been positioned on the implant for some time (e.g. one day to one week), it can be expedited to just a few minutes by dipping the bottom 311 of the cap 310 in gingival retraction chemicals which results in the gingiva tightening and pulling away from the implant 350. Thus, the ring-shaped cavity is created due to the mechanical action of the cap 310 and the chemical action of the gingiva retraction chemical. Furthermore, it is possible to produce the cap 310 or just its bottom 311 from a porous material to enhance the ability of the cap to retain the gingival retraction chemical prior to its release into the gingival tissue.

Figure 25:
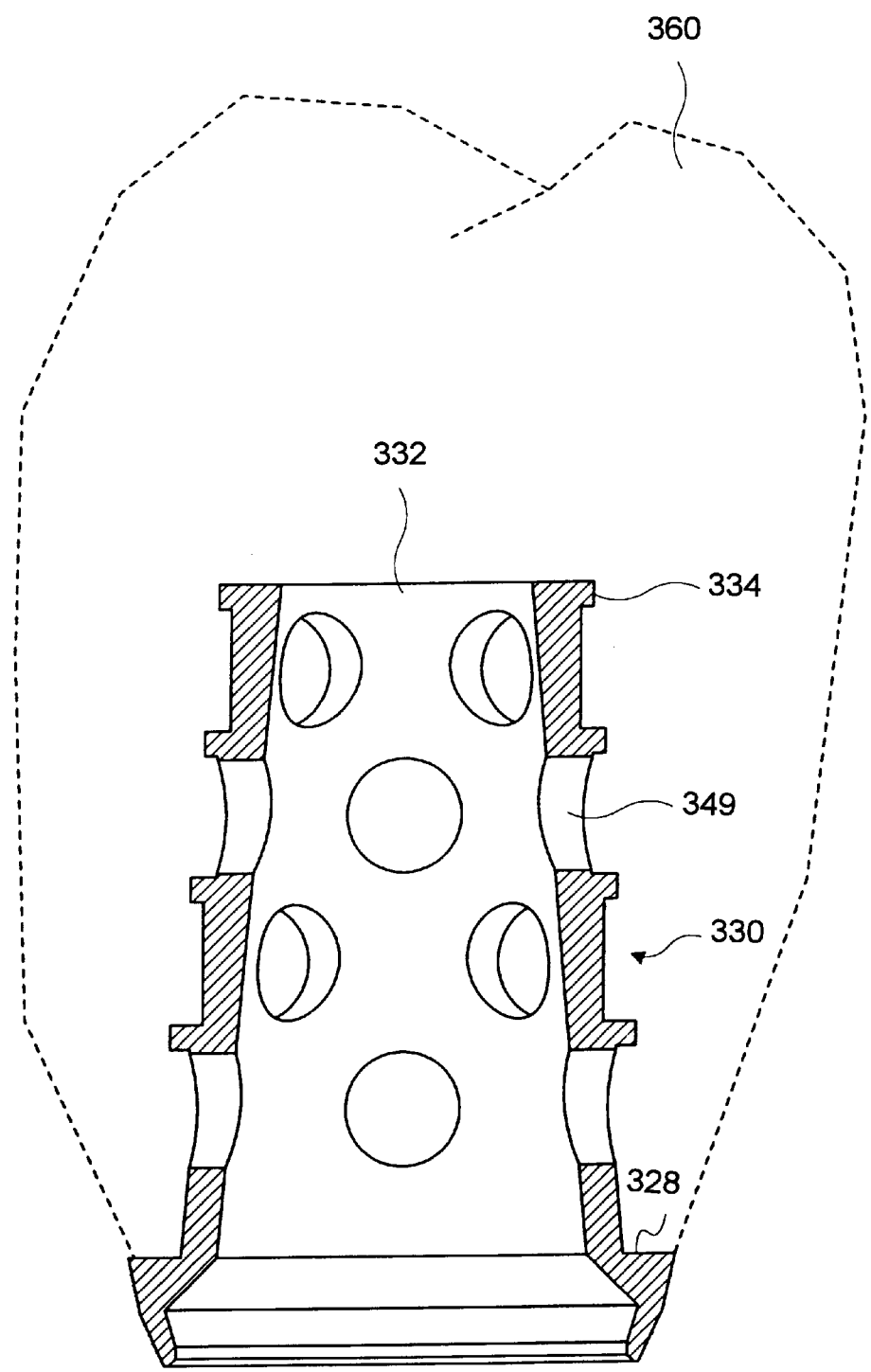
FIG. 25 is the same sectional view of the cap as in FIG. 23 with the addition of a diagrammatic illustration of an artificial tooth shell around the cap.

To achieve a temporary tooth that is cosmetically pleasing and can last for several months, the cap 330 of FIGS. 22–23 should be used, as is illustrated in FIG. 24. An appropriately-shaped shell 360, chosen to mimic the tooth being restored, is filled (wholly or partially as desired) with a quantity of a dental plastic material (e.g., acrylic) that hardens slowly, and the "filled" shell is placed over the cap as is illustrated in FIG. 25, and manipulated to force the plastic material (not shown in FIG. 25) through the perforations 349 into contact with the post 356. The spaces between the shell 360 and the cap 330, and between the cap 330 and the post 356 (not shown in FIG. 25) will be filled with the hardening plastic material. In practice, the clinician preparing the temporary tooth will gently seat and remove the shell 360 and the cap 330 with the hardening material around the post 356 while the plastic material hardens. When the plastic material has hardened, that person will remove this assembly from the post for final preparation of the temporary tooth. If the tooth is being prepared in patient's mouth where the site has one or two adjacent teeth, it may be desired to remove the rim 333 of the cap 330 from the implant 350, at least until preparation of the tooth is completed. If the tooth is being prepared on a model outside the patient's mouth, where the site can be isolated, the rim 333 can be usefully retained, because the final temporary tooth need not extend below the implant rim 354 (and the hardening of the temporary tooth material around the cap 330 may reduce the flexibility of the rim 333). In either case, in the final preparation of the tooth, the shell 360 may be removed and the hardened plastic material may be shaped and polished, and then cemented in place on the post 356 with a suitable dental cement. It will be appreciated that FIG. 25 is not drawn to scale. In practice, the shell may be closer to the post than this illustration shows it. While no acrylic (or other suitable tooth-forming material) has been illustrated, such materials are well-known in the dental art.

The cap 330 may be adjusted in length to match the length of the post 356 by cutting the cap 330 at the top of any of the intermediate rims 336, 338 or 340. FIG. 24 shows a post 356 which extends to the uppermost rim 334 at the top opening 332. If a shorter post is used, the cap 330 can be shortened to match the post by removing that portion of the cap 330 above the first rim 340 beyond the top of post. Preferably, the rims 336, 338 and 340 would be positioned to correspond to the common sizes in which posts are available.

The invention is not limited to the physical configurations of the implant and the caps that are illustrated herein by way of example. The dental arts include a wide variety of implants and posts and abutments designed for use with them. The invention is intended to apply to all such to which it can be adapted.

What is claimed is:

1. A dental implant for implantation in living jawbone having overlying gingiva, comprising:
    a generally cylindrical body section having an exterior surface for confronting said jawbone;
    a head section attached to said body section for extending through said overlying gingiva when said body section is confronting said jawbone, said head section having an end portion which is adapted to be positioned near an outer layer of said gingiva; and
    a bore within said head section extending to an opening at said end portion of said head section, said bore being defined by first, second, and third walls, said first wall having internal threads, said second wall having a larger diameter than said first surface and being substantially cylindrical, said second wall extending from said first wall toward said end portion, said third wall extending from said second wall to said opening, said third wall flaring toward said opening to a diameter that is wider than a diameter of said second wall said second wall including an internally threaded section such that said bore has two distinct internally threaded sections.

2. The dental implant of claim 1, wherein said internally threaded section of said second wall includes at least one thread groove, said at least one groove separating lands on said second wall.

3. The dental implant of claim 2, wherein said lands preserve a major portion of said second wall.

4. The dental implant of claim 2, wherein said thread grooves form a multi-lead thread.

5. The dental implant of claim 4, wherein a pitch of said thread grooves is approximately one millimeter.

6. The dental implant of claim 1, wherein said head section flares outwardly from said main body toward said end portion.

7. The dental implant of claim 6, wherein said exterior surface of said main body section is threaded and said head section has a smooth external surface.

8. The dental implant of claim 1, wherein said bore extends into said body section.

9. The dental implant of claim 8, wherein said first wall is entirely within said body section.

10. The dental implant of claim 8, wherein said third wall is entirely within said head section.

11. The dental implant of claim 10, wherein said second wall is entirely within said head section.

12. The dental implant of claim 1, wherein said end portion of said head section includes a generally annular surface that is at an angle with respect to a central axis of said implant, said angle being substantially less that 90°.

13. The dental implant of claim 12, wherein said end portion further includes a non-round fitting adjacent to said annular surface.

14. The dental implant of claim 12, wherein said angle is approximately 45°.

15. The dental implant of claim 1, wherein said exterior surface of said main body section is roughened and said head section has a smooth external surface.

16. The dental implant of claim 1, wherein said flaring of said third wall is at angle suitable to provide a locking taper for engagement with a corresponding taper on a mating component.

17. A system for delivering an implant into living bone comprising:
    an implant having an exterior surface for confronting said living bone and including a bore that has an opening at an end portion of said implant, said bore being at least partially defined by a substantially cylindrical section;
    a carrier device having an expandable portion and a non-round fitting, said expandable portion being inserted to said substantially cylindrical section of said bore of said implant, said non-round fitting being accessible near said end portion of said implant; and
    means for expanding said expandable cylindrical segment into tight engagement with said substantially cylindrical section of said bore.

18. The implant delivery system of claim 17, wherein said bore further includes a threaded section positioned below said cylindrical segment.

19. The implant delivery system of claim 18, wherein said bore further includes a flared section positioned above said cylindrical section.

20. The implant delivery system of claim 17, wherein said substantially cylindrical section has an uninterrupted circular cross-section.

21. The implant delivery system of claim 17, wherein said expandable portion includes a plurality of fingers having radial extremities which reside on a generally circular locus.

22. The implant delivery system of claim 21, wherein a diameter of said generally circular locus is slightly less than a diameter of said substantially cylindrical section prior to the actuation of said expanding means.

23. The implant delivery system of claim 17, wherein said carrier has a hollow section within said expandable portion, said expanding means includes a structure inserted into said hollow section.

24. The implant delivery system of claim 23, wherein said hollow section includes internal threads and said structure has outer threads for threadably engaging said internal threads of said hollow structure.

25. The implant delivery system of claim 24, wherein said hollow section includes wedge blocks for engaging an end of said structure.

26. The implant delivery system of claim 17, wherein said carrier includes a radially extending flange between said non-round fitting and said expandable portion for engaging said end portion of said implant.

27. The implant delivery system of claim 26, wherein said end portion includes a generally annular surface that is at an angle with respect to a central axis of said implant, said angle being less substantially less that 90°, said radially extending flange has a surface cooperating with said generally annular surface.

28. The implant delivery system of claim 17, wherein said generally cylindrical wall includes thread grooves separated by lands on said generally cylindrical wall.

29. The implant delivery system of claim 28, wherein said expandable portion has threads which mate with said thread grooves.

30. The implant delivery system of claim 28, wherein said bore has a second threaded section of a different diameter than said first threaded region for engaging fasteners holding artificial dentition on said implant.

31. A system for delivering an implant into living bone comprising:
   an implant having an exterior surface for confronting said living bone and including a bore that has an opening at an end portion of said implant, said bore being at least partially defined by a threaded section;
   a carrier device having an expandable threaded portion and a non-round fitting, said expandable threaded portion being threadably inserted into said threaded section of said bore of said implant, said non-round fitting being accessible near said end portion of said implant; and
   means for expanding said expandable threaded segment into tight engagement with said threaded section of said bore.

32. The implant delivery system of claim 31, wherein said threaded section is formed by multi-lead threads.

33. The implant delivery system of claim 32, wherein a pitch of said threaded section is approximately one millimeter.

34. The implant delivery system of claim 31, wherein a torque required to threadably insert said expandable threaded portion into said threaded section of said bore is less about 10 N-cm prior to actuation of said expanding means.

35. The implant delivery system of claim 31, wherein said non-round fitting is capable of receiving about 40 N-cm of torque while said implant is held non-rotationally without significant movement of said expandable threaded portion relative to said threaded section due to said tight engagement of said expanding means.

36. The implant delivery system of claim 35, wherein said non-round fitting is capable of receiving 100 N-cm of torque while said implant is held non-rotationally without significant movement of said expandable threaded portion relative to said threaded section due to said tight engagement.

37. The implant delivery system of claim 31, wherein said expandable threaded portion is fully inserted into said threaded section in approximately one turn.

38. The implant delivery system of claim 31, wherein said carrier has a hollow section within said expandable portion, said expanding means includes a structure inserted into said hollow section.

39. The implant delivery system of claim 38, wherein said hollow section includes internal threads and said structure has outer threads for threadably engaging said internal threads of said hollow structure.

* * * * *

UNITED STATES PATENT AND TRADEMARK OFFICE
CERTIFICATE OF CORRECTION

PATENT NO. : 6,217,331 B1  
DATED : April 17, 2001  
INVENTOR(S) : Rogers et al.

Page 1 of 1

It is certified that error appears in the above-identified patent and that said Letters Patent is hereby corrected as shown below:

Title page,
Item [56], OTHER PUBLICATIONS, third reference (Sutter et al.), delete "Desing" and insert -- Design --

Column 13, claim 1,
Line 61, after "wall" insert -- , --

Column 14, claim 12,
Line 24, delete "that" and insert -- than --

Column 14, claim 16,
Line 34, after "at" insert -- an --

Column 15, claim 27,
Line 17, delete "that" and insert -- than --

Column 16, claim 34,
Line 12, after "less" insert -- than --

Signed and Sealed this

Nineteenth Day of February, 2002

*Attest:*

JAMES E. ROGAN
*Attesting Officer*     Director of the United States Patent and Trademark Office